US009261468B2

(12) United States Patent
Bingham et al.

(10) Patent No.: US 9,261,468 B2
(45) Date of Patent: Feb. 16, 2016

(54) MULTI-PARTICLE INSPECTION USING ASSOCIATED PARTICLE SOURCES

(71) Applicant: UT-Battelle, LLC, Oak Ridge, TN (US)

(72) Inventors: Philip R. Bingham, Knoxville, TN (US); John T. Mihalczo, Oak Ridge, TN (US); James A. Mullens, Farragut, TN (US); Seth M. McConchie, Knoxville, TN (US); Paul A. Hausladen, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 208 days.

(21) Appl. No.: 13/801,695

(22) Filed: Mar. 13, 2013

(65) Prior Publication Data

US 2013/0264486 A1  Oct. 10, 2013

Related U.S. Application Data

(63) Continuation-in-part of application No. 12/804,549, filed on Jul. 23, 2010, now Pat. No. 8,586,939.

(60) Provisional application No. 61/610,162, filed on Mar. 13, 2012.

(51) Int. Cl.
*G01N 23/05* (2006.01)
*G01V 5/00* (2006.01)

(52) U.S. Cl.
CPC .............. *G01N 23/05* (2013.01); *G01V 5/0008* (2013.01); *G01V 5/0033* (2013.01)

(58) Field of Classification Search
CPC .... G01V 5/0008; G01V 5/0033; G01N 23/05
See application file for complete search history.

(56) References Cited

U.S. PATENT DOCUMENTS

| 4,897,550 A | 1/1990 | Bernard et al. |
| 5,247,177 A * | 9/1993 | Goldberg ............. G01N 23/066 250/358.1 |

(Continued)

FOREIGN PATENT DOCUMENTS

| GB | 2166280 | 4/1986 |
| WO | WO 2004/029601 | 4/2004 |
| WO | WO 2009/143131 | 11/2009 |

OTHER PUBLICATIONS

Aleksandrov et al., "Application of neutron generators for high explosives, toxic agents and fissile material detection," *Applied Radiation and Isotopes*, vol. 63, pp. 537-543 (Jul. 2005).

(Continued)

*Primary Examiner* — David Porta
*Assistant Examiner* — Mindy Vu
(74) *Attorney, Agent, or Firm* — Klarquist Sparkman, LLP

(57) ABSTRACT

Disclosed herein are representative embodiments of methods, apparatus, and systems for performing combined neutron and gamma ray radiography. For example, one exemplary system comprises: a neutron source; a set of alpha particle detectors configured to detect alpha particles associated with neutrons generated by the neutron source; neutron detectors positioned to detect at least some of the neutrons generated by the neutron source; a gamma ray source; a set of verification gamma ray detectors configured to detect verification gamma rays associated with gamma rays generated by the gamma ray source; a set of gamma ray detectors configured to detect gamma rays generated by the gamma ray source; and an interrogation region located between the neutron source, the gamma ray source, the neutron detectors, and the gamma ray detectors.

18 Claims, 13 Drawing Sheets

(56) References Cited

U.S. PATENT DOCUMENTS

| | | | |
|---|---|---|---|
| 5,591,967 A * | 1/1997 | Moake | 250/252.1 |
| 5,600,303 A | 2/1997 | Husseiny et al. | |
| 5,692,029 A | 11/1997 | Husseiny et al. | |
| 6,297,507 B1 | 10/2001 | Chen et al. | |
| 6,858,848 B1 * | 2/2005 | Tickner | G01N 23/20 250/363.03 |
| 6,922,455 B2 | 7/2005 | Jurczyk et al. | |
| 7,023,956 B2 | 4/2006 | Heaton et al. | |
| 7,405,409 B2 | 7/2008 | Kearfott | |
| 7,461,032 B2 | 12/2008 | Heaton et al. | |
| 7,999,233 B1 * | 8/2011 | Derenzo | 250/360.1 |
| 8,586,939 B2 | 11/2013 | Bingham et al. | |
| 2003/0165213 A1 | 9/2003 | Maglich | |
| 2006/0065832 A1 * | 3/2006 | Orr | 250/336.1 |
| 2008/0017804 A1 | 1/2008 | Krishnamoorthy et al. | |
| 2008/0251735 A1 | 10/2008 | Putterman et al. | |
| 2008/0302968 A1 | 12/2008 | Tadokoro et al. | |
| 2009/0078881 A1 | 3/2009 | Dangendorf et al. | |
| 2009/0114834 A1 | 5/2009 | Pekarsky | |
| 2010/0019160 A1 | 1/2010 | Wallace | |

OTHER PUBLICATIONS

Beyerle et al., "Design of an associated particle imaging system," *Nuclear Instruments and Methods in Physics Research*, vol. 299, Issues 1-3, pp. 458-462 (Dec. 1990).

Bystritsky et al., "Study of the Associated Particle Imaging technique for the hidden explosives identification," *Proc. Of the Int'l Conf. On Requirements and Technologies for the Detection, Removal and Neutralization of Landmines and UXO, EUDEM2-SCOT-2003*, 15 pp. (Sep. 2003).

Carriveau, "Associated Particle Imaging: An Enabling Technology of Detection Improvised Explosives," *Detention and Disposal of Improvised Explosives*, pp. 123-125 (Jun. 2006).

Cooper et al., "Evaluation of ZnO(Ga) Coatings as Alpha Particle Transducers Within a Neutron Generator," Y-12 National Security Complex Technical Report, 8 pp. (document dated May 2002).

Hausladen et al., "Passive and Active Fast-Neutron Imaging in Support of AFCI Safeguards Campaign," Oak Ridge National Laboratory Technical Report, 15 pp. (document dated Aug. 2009).

Hausladen et al., "Portable fast-neutron radiography with the nuclear materials identification system for fissile material transfers," *Nuclear Instruments and Methods in Physics Research B*, vol. 261, pp. 387-390 (Apr. 2007).

Hurley et al., "A Review of the Associated Particle Imaging Technique," *Int'l Conf. On the Application of Accelerators in Research and Industry*, pp. 1-7 (Nov. 1992).

Keegan et al., "Identification of Fissionable Materials Using the Tagged Neutron Technique," *Trans. of the American Nuclear Society*, 2 pp. (Jun. 2009).

Loschke, "Photon Signatures for Standoff Bomb Detection," Master of Science Thesis, 59 pp. (Aug. 2008).

Petö, "Prospects of Imaging by Associated Particle Timing with D + D and D + T Neutrons," *Appl. Radiat. Isot.*, vol. 49, No. 5/6, pp. 553-554 (May 1998).

Reichardt et al., "Small, Portable, Lightweight DT Neutron Generator for Use with NMIS," Y-12 National Security Complex Technical Report, 7 pp. (document dated Jun. 2001).

Rhodes et al., "Associated-Particle Sealed-Tube Neutron Probe for Nonintrusive Inspection," *Int'l Conf. on the Application of Accelerators in Research and Industry*, 4 pp. (Dec, 1996).

Tardocchi et al., "YAP scintillators for resonant detection of epithermal neutrons at pulsed neutron sources," *Rev. Sci. Instrum.*, vol. 75, No. 11, pp. 4880-4890 (Nov. 2004).

Tinsley et al., "Mobile associated particle imaging system," *SPIE*, vol. 2859, pp. 102-106 (Jul. 1996).

Ussery et al., "Design and Development of the Associated-Particle Three-Dimensional Imaging Technique," Los Alamos National Laboratory Technical Report, 20 pp. (Oct. 1994).

* cited by examiner

MULTI-PARTICLE INSPECTION USING ASSOCIATED PARTICLE SOURCES

CROSS REFERENCE TO RELATED APPLICATIONS

This application claims the benefit of U.S. Provisional Application No. 61/610,162 filed on Mar. 13, 2012 and entitled "MULTI-PARTICLE INSPECTION USING ASSOCIATED PARTICLE SOURCE". This application is also a continuation-in-part of U.S. application Ser. No. 12/804,549 filed on Jul. 23, 2010, and entitled "MULTIPLE SOURCE ASSOCIATED PARTICLE IMAGING FOR SIMULTANEOUS CAPTURE OF MULTIPLE PROJECTIONS".

ACKNOWLEDGMENT OF GOVERNMENT SUPPORT

This invention was made with government support under Contract No. DE-AC05-00OR22725 awarded by the U.S. Department of Energy. The government has certain rights in the invention.

FIELD

The present application concerns neutron radiography systems and techniques.

BACKGROUND

Neutrons have several properties that make them useful in detecting and imaging concealed objects. For example, neutrons have excellent penetrating power, including the ability to easily penetrate metal objects and concrete. Additionally, neutrons interact with certain materials (e.g., nitrogen-rich materials) in a well-known, predictable manner. To take advantage of these properties, neutron radiography systems have been developed. Conventional neutron radiography systems, however, suffer from a number of disadvantages. For example, scattered neutrons are a significant source of noise in conventional neutron radiography systems. To reduce the noise caused by scattered neutrons, conventional systems use physical collimation to shape the neutrons emitted from the neutron source into a thin fan. Limiting the neutrons to a thin fan helps prevent neutrons emitted from outside of the imaging plane (typically defined by a single row of neutron detectors) from scattering back into the image as noise, but prevents the system from having a wide field of view. Furthermore, conventional neutron radiography systems are limited to using a single neutron source, as any additional neutron source would create an impermissible amount of noise in the imaging plane. As a consequence of using a single neutron source, which is typically collimated into a thin fan, the image generation process is extremely slow. Conventional neutron radiography systems are therefore not well suited for applications that demand fast image processing (e.g., commercial cargo screening). Accordingly, there exists a need for improved neutron radiography systems.

SUMMARY

Disclosed below are representative embodiments of methods, apparatus, and systems for performing neutron radiography or aspects thereof. The disclosed embodiments should not be construed as limiting in any way. Instead, the present disclosure is directed toward all novel and nonobvious features and aspects of the various disclosed embodiments, alone and in various combinations and subcombinations with one another. The disclosed methods, apparatus, and systems are not limited to any specific aspect or feature or combination thereof, nor do the disclosed embodiments require that any one or more specific advantages be present or problems be solved.

One of the exemplary embodiments disclosed herein is a neutron radiography system comprising a first neutron source and a first array of one or more alpha particle detectors configured to detect alpha particles associated with neutrons generated by the first neutron source. The system further comprises a second neutron source and a second array of one or more alpha particle detectors configured to detect alpha particles associated with neutrons generated by the second neutron source. The system further comprises one or more neutron detectors that are positioned to detect at least some of the neutrons generated by the first neutron source and the second neutron source. The exemplary system also includes an interrogation region located between the first neutron source, the second neutron source, and the one or more neutron detectors. The neutrons generated by the first neutron source and the neutrons generated by the second neutron source can be uncollimated and form neutron cone beams. The neutrons from the first neutron source and the neutrons from the second neutron source can also be monoenergetic. In certain implementations, the system further comprises an image processing system coupled to the first array of one or more alpha particle detectors, the second array of one or more alpha particle detectors, and the one or more neutron detectors. The image processing system can be configured to generate an image of an object positioned in the interrogation region based at least in part on the observed number of neutrons detected by the one or more neutron detectors relative to an expected number of neutrons detected by the one or more neutron detectors in the absence of the object. The image processing system can also be configured to generate an image of an object positioned in the interrogation region based at least in part on a first projection image generated using detected neutrons from the first neutron source and a second projection image generated using detected neutrons from the second neutron source. When an object is disposed in the interrogation region, at least one of the first neutron source or the second neutron source can be located adjacent to a corner of the object. Furthermore, the one or more neutron detectors can be arranged into a variety of shapes and configuration. For example, the one or more neutron detectors can be at least partially arranged into a curved shape. Additionally, the one or more neutron detectors can be arranged in a ring shape. In certain implementations (e.g., when the one or more neutron detectors are arranged in a ring shape) the second neutron source can be positioned between the first neutron source and the first array of one or more alpha particle detectors. The first neutron source can be configured to emit a first neutron cone beam in a first orientation and the second neutron source can be configured to emit a second cone beam in a second orientation, the first orientation being different than the second orientation. For example, the second orientation can be 90 degrees or substantially 90 degrees from the first orientation. In some implementations, at least one of the first neutron source or the second neutron source has a cone-beam angle of 45 degrees or greater. The exemplary system can further comprise one or more additional neutron sources. The exemplary system can also be part of an imaging system that includes a gamma-ray imaging system.

Also disclosed herein are exemplary methods for performing neutron radiography. For example, in one exemplary method, an object is interrogated with a plurality of neutrons, which includes a first portion of neutrons generated from a first neutron source and a second portion of neutrons generated from a second neutron source. Further, at least some of the first portion and the second portion are generated during a same time period. One or more neutrons from the first portion and one or more neutrons from the second portion are detected, and an image of the object is generated based at least in part on the detected neutrons from the first portion and the detected neutrons from the second portion. The first neutron source and the second neutron source can be uncollimated. Further, the first portion of neutrons can be from a first cone beam of neutrons emitted from the first neutron source and the second portion of neutrons can be from a second cone beam of neutrons emitted from the second neutron source, where the first cone beam of neutrons and the second cone beam do not overlap at their respective origins. The act of generating the image of the object can further comprise generating projection images from the detected neutrons from the first portion and from the detected neutrons from the second portion, the projection images including a first projection image associated with the detected neutrons from the first portion and a second projection image associated with the detected neutrons from the second portion, and reconstructing the image of the object using at least the first projection image and the second projection image. The act of reconstructing the image can be performed using a variety of techniques, such as a maximum likelihood estimation maximization, ordered subset estimation maximization, filtered back projection, or iterative reconstruction technique.

In another exemplary method disclosed herein, a first neutron and a first associated particle at a first neutron source are generated as well as a second neutron and a second associated particle at a second neutron source. The first associated particle is detected at a first position on a first associated particle detector and the second associated particle is detected at a second position on a second associated particle detector. A first path of the first neutron through an interrogated object and a second path of the second neutron through the interrogated object are determined. In this embodiment, the determination of the first path of the first neutron is based at least in part on the first position at which the first associated particle is detected on the first associated particle detector, and the determination of the second path of the second neutron is based at least in part on the second position at which the second associated particle is detected on the second associated particle detector. Additionally, the first neutron is detected at a first neutron detector, and the second neutron at a second neutron detector. In certain implementations, the first neutron detector and the second neutron detector are part of a single array of neutron detectors. In certain implementations, the associated particle is an alpha particle. In such implementations, the first associated particle detector can be a first alpha particle detector, and the second associated particle detector can be a second alpha particle detector. In particular exemplary uses, the first neutron is detected at the first neutron detector simultaneously or substantially simultaneously as the second neutron is detected at the second neutron detector. In such instances, the first neutron can be discriminated from the second neutron based at least in part on the determination of the first path of the first neutron and the determination of the second path of the second neutron. In some implementations, the detection of the first neutron is used in part to generate a first projection image, and the detection of the second neutron is used in part to generate a second projection image different than the first projection image. Furthermore, the first neutron source and the second neutron source can be operated simultaneously to generate neutrons during a common time period.

Some of the disclosed methods (e.g., the image processing methods) can be implemented using computer-executable instructions stored on one or more computer-readable media and executed on a computer. Any of the intermediate or final data created and used during implementation of the disclosed methods or systems can also be stored on one or more computer-readable media. For example, one exemplary embodiment disclosed herein comprises one or more computer-readable media storing computer-executable instructions which when executed by a computer cause the computer to perform a method. In this embodiment, the method comprises receiving data from two or more alpha particle detectors, including data from a first alpha particle detector indicating times at which a first set of alpha particles are detected by the first alpha particle detector (the first set of alpha particles being associated with a first set of neutrons generated by a first neutron source) and data from a second alpha particle detector indicating times at which a second set of alpha particles are detected by the second alpha particle detector (the second set of alpha particles being associated with a second set of neutrons generated by a second neutron source). The method further comprises receiving data from one or more neutron detectors indicating times at which neutrons are detected by the one or more neutron detectors, and identifying the neutrons detected by the one or more neutron detectors as being either neutrons emitted from the first neutron source or neutrons emitted from the second neutron source based at least in part on the data from the first alpha particle detector and the data from the second alpha particle detector. The method can further comprise generating projection images based at least in part on the data from the two or more associated particle detectors and the data from the one or more neutron detectors, the projection images including a first projection image based on neutrons detected at the one or more neutron detectors and identified as being from the first set of neutrons emitted from the first neutron source, and a second projection image based on neutrons detected at the one or more neutron detectors and identified as being from the second set of neutrons emitted from the second neutron source. The method can also comprise generating a three-dimensional image of the object using at least the first projection image and the second projection image. In certain implementations, the data from the first alpha particle detector further indicates positions on the first alpha particle detector at which the first set of alpha particles are detected, and the data from the second alpha particle detector further indicates positions on the second alpha particle detector at which the second set of alpha particles are detected. In such implementations, the method can further comprise identifying two neutrons simultaneously detected by the one or more neutron detectors as being a neutron emitted from the first neutron source and a neutron emitted from the second neutron source based at least in part on the data from the first alpha particle detector and the data from the second alpha particle detector. In certain implementations, the first set of neutrons and the second set of neutrons are generated at least partially during a same time period.

Another exemplary embodiment disclosed herein is an imaging system, comprising a neutron source; an array of one or more alpha particle detectors configured to detect alpha particles associated with neutrons generated by the neutron source; one or more neutron detectors positioned to detect at least some of the neutrons generated by the neutron source; a gamma ray source; one or more gamma ray detectors configured to detect at least some of the gamma rays generated by the gamma ray source; and an interrogation region located between the neutron source, the gamma ray source, the one or more neutron detectors, and the one or more gamma ray detectors. In certain implementations, the neutron source is a first neutron source, the array of one or more alpha particle detectors is a first array of one or more alpha particle detectors. In such implementations, the system can further comprise a second neutron source; and a second array of one or more alpha particle detectors configured to detect alpha particles associated with neutrons generated by a second neutron source. In some implementations, the imaging system further comprises an array of one or more verification gamma ray detectors configured to detect verification gamma rays associated with gamma rays generated by the gamma ray source. In further implementations, the gamma ray source is a first gamma ray source, the array of one or more verification gamma ray detectors is a first array of one or more verification gamma ray detectors, and the imaging system further comprises a second gamma ray source and a second array of one or more verification gamma ray detectors configured to detect verification gamma rays generated by the second gamma ray source. In some implementations, the imaging system further comprises an image processing system coupled to the array of one or more alpha particle detectors, the one or more neutron detectors, the array of one or more verification gamma ray detectors, and the one or more gamma ray detectors. The image processing system can be configured to generate an image of an object positioned in the interrogation region. The generated image can be based at least in part on the observed number of tagged neutrons detected by the one or more neutron detectors and the observed number of tagged gamma rays detected by the one or more gamma ray detectors.

A further exemplary embodiment disclosed herein is a method that comprises: interrogating an object with a plurality of neutrons and a plurality of gamma rays, at least some of the neutrons and gamma rays being generated during a same time period; detecting one or more neutrons and one or more gamma rays; and generating an image of the object based at least in part on the detected neutrons and the detected gamma rays. In certain implementations, a first portion of the neutrons is generated from a first neutron source and a second portion of the neutrons is generated from a second neutron source (e.g., uncollimated neutron sources). In some implementations, a first portion of the gamma rays is generated from a first gamma ray source and a second portion of the gamma rays is generated from a second gamma ray source. The act of generating the image of the object can comprise generating projection images from the detected neutrons and the detected gamma rays, the projection images can include a first projection image generated from the detected neutrons and a second projection image generated from the gamma rays.

Another exemplary method disclosed herein comprises: generating, at a gamma emission source, a gamma emission and a verification gamma emission associated with the gamma emission; detecting the verification gamma emission at a position on a verification gamma emission detector; generating, at a neutron source, a neutron and an associated particle; detecting the associated particle at a position on a verification gamma emission detector; detecting the gamma emission at a gamma emission detector; detecting the neutron at a neutron detector; and determining a path of the gamma emission through an interrogated object and a path of the neutron through the interrogated object, the determination of the path of the gamma emission being based on the position at which the verification gamma emission is detected on the verification gamma emission detector, and the determination of the path of the neutron being based on the position at which the associated particle is detected on the associated particle detector. In certain implementations, the gamma emission is a first gamma emission, the verification gamma emission is a first verification gamma emission, the gamma emission source is a first gamma emission source, and the path of the gamma emission through the interrogated object is a first path of the gamma emission. In such implementations, the method can further comprise generating a second gamma emission and a second verification gamma emission associated with the second gamma emission at a second gamma emission source, the second gamma emission source being different than the first gamma emission source; and detecting the second verification gamma emission at a position on a second verification gamma emission detector, the second verification gamma emission detector being different than the first verification gamma emission detector. In some implementations, the method further comprises determining a path of the second gamma emission through the interrogated object, the determination of the path of the second gamma emission being based on the position at which the second verification gamma emission is detected on the second verification gamma emission detector. Still further, the first gamma emission, the second gamma emission, and the neutron can be detected at the same time or substantially the same time. In certain implementations, the neutron is a first neutron, the associated particle is a first associated particle, the neutron source is a first neutron source, and the path of the neutron is the first path of the first neutron. In these implementations, the method further comprises generating a second neutron and a second associated particle at a second neutron source, the second neutron source being different than the first neutron source; and detecting the second associated particle at a position on a second associated particle detector, the second associated particle detector being different than the first associated particle detector. In certain implementations, the method further comprises determining a second path of the second neutron through the interrogated object, the determination of the second path of the second neutron being based on the position at which the second associated particle is detected on the second associated particle detector. Further, the gamma emission, the first neutron, and the second neutron can be detected at the same time or substantially the same time. In some implementations, the gamma emission detector and the neutron detector are part of a single array of detectors.

As noted, some of the disclosed methods (e.g., the image processing methods) can be implemented using computer-executable instructions stored on one or more computer-readable media and executed on a computer. For example, one exemplary embodiment disclosed herein comprises one or more computer-readable media storing computer-executable instructions which when executed by a computer cause the computer to perform a method. In this embodiment, the method comprises: (a) in connection with a tagged neutron system, receiving data from two or more alpha particle detectors, including data from a first alpha particle detector indicating times at which a first set of alpha particles are detected by the first alpha particle detector and data from a second alpha particle detector indicating times at which a second set of alpha particles are detected by the second alpha particle detector, wherein the first set of alpha particles are associated with a first set of neutrons generated by a first neutron source, and wherein the second set of alpha particles are associated with a second set of neutrons generated by a second neutron source; receiving data from one or more neutron detectors indicating times at which neutrons are detected by the one or more neutron detectors; identifying the neutrons detected by the one or more neutron detectors as being either neutrons emitted from the first neutron source or neutrons emitted from the second neutron source based at least in part on the data from the first alpha particle detector and the data from the second alpha particle detector; and (b) in association with a tagged gamma emission system, receiving data from two or more verification gamma emission detectors, including data from a first verification gamma emission detector indicating times at which a first set of verification gamma emissions are detected by the first verification gamma emission detector and data from a second verification gamma emission detector indicating times at which a second set of verification gamma emissions are detected by the second verification gamma emission detector, wherein the first set of verification gamma emissions are associated with a first set of picturization gamma emissions generated by a first gamma emission source, and wherein the second set of verification gamma emissions are associated with a second set of picturization gamma emissions generated by a second gamma emission source; receiving data from one or more picturization gamma emission detectors indicating times at which picturization gamma emissions are detected by the one or more gamma emission detectors; and identifying the picturization gamma emission detected by the one or more picturization gamma emission detectors as being either picturization gamma emissions emitted from the first gamma emission source or picturization gamma emissions emitted from the second gamma emission source based at least in part on the data from the first verification gamma emission detector and the data from the second verification gamma emission detector. The first set of neutrons, the second set of neutrons, the first set of picturization gamma emissions, and the second set of picturization gamma emission can all be generated at least partially during a same time period and are used to interrogate an object being imaged during the same time period.

The foregoing and other objects, features, and advantages of embodiments of the invention will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

I. General Considerations

Figure 1:
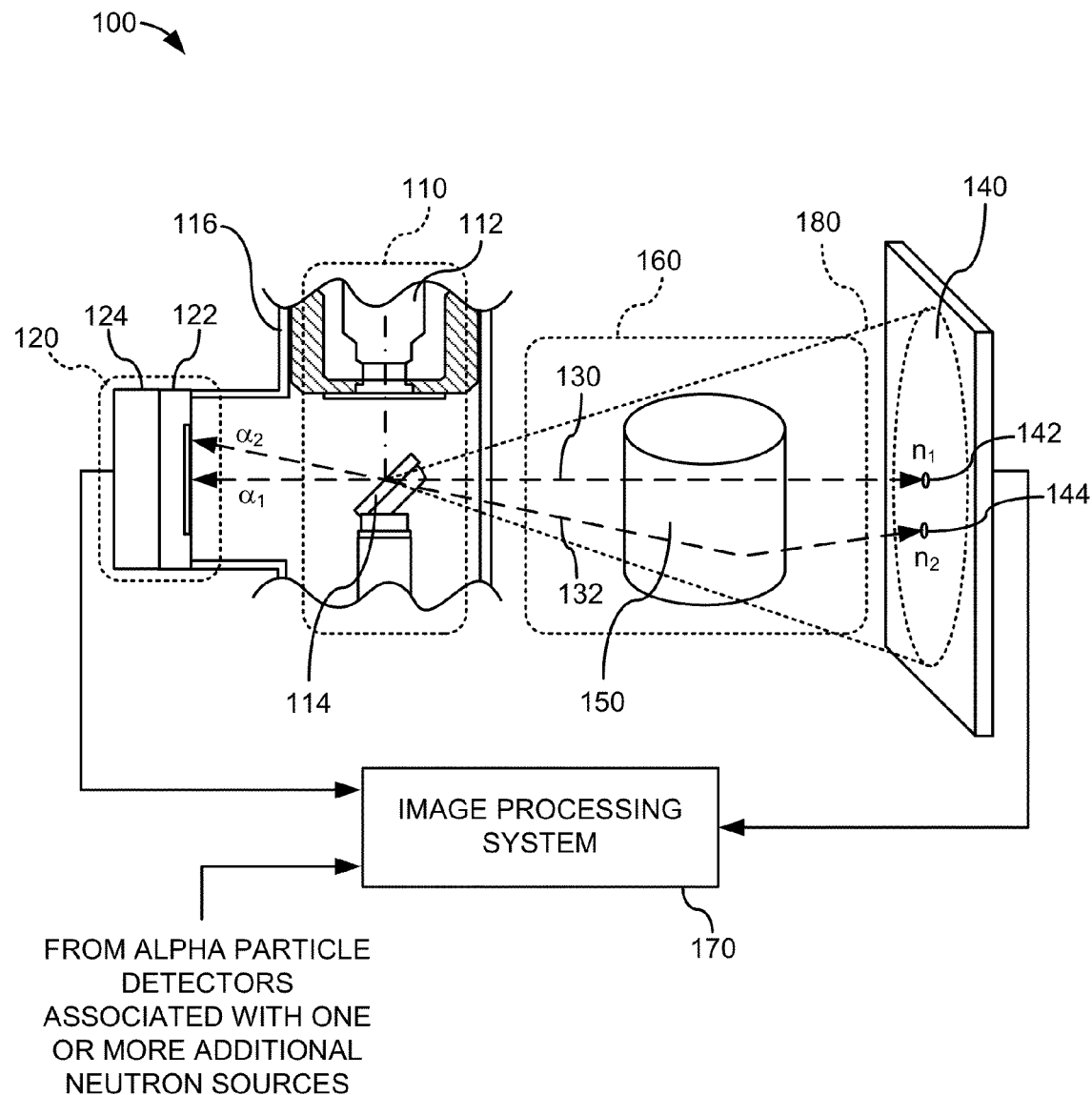
FIG. 1 is a schematic block diagram of a first associated particle neutron radiography ("APNR") system according to an embodiment of the disclosed technology.

Disclosed below are representative embodiments of methods, apparatus, and systems for performing neutron radiography. The disclosed methods, apparatus, and systems should not be construed as limiting in any way. Instead, the present disclosure is directed toward all novel and nonobvious features and aspects of the various disclosed embodiments, alone and in various combinations and subcombinations with one another. The disclosed methods, apparatus, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, apparatus, and systems can be used in conjunction with other methods, apparatus, and systems.

Some of the disclosed methods (e.g., the image processing methods) can be implemented using computer-executable instructions stored on one or more computer-readable media (e.g., non-transitory computer-readable media, such as one or more optical media discs, volatile memory components (e.g., DRAM or SRAM), or nonvolatile memory or storage components (e.g., hard drives)) and executed on a computer (e.g., any commercially available computer or a computer processor embedded in image processing equipment associated with embodiments of the disclosed technology). Any of the intermediate or final data created and used during implementation of the disclosed methods or systems can also be stored on one or more computer-readable media (e.g., non-transitory computer-readable media).

For clarity, only certain selected aspects of the software-based embodiments are described. Other details that are well known in the art are omitted. For example, it should be understood that the software-based embodiments are not limited to any specific computer language or program. Likewise, embodiments of the disclosed technology are not limited to any particular computer or type of hardware. Exemplary computing environments suitable for performing any of the disclosed software-based methods are introduced in Section IV below.

The disclosed methods can also be implemented using specialized computing hardware that is configured to perform any of the disclosed methods. For example, the disclosed methods can be implemented by an integrated circuit (e.g., an application specific integrated circuit ("ASIC"), a graphics processing unit ("GPU"), or programmable logic device ("PLD"), such as a field programmable gate array ("FPGA")) specially designed to implement any of the disclosed methods (e.g., dedicated hardware configured to perform any of the disclosed image processing techniques).

II. Introduction to the Disclosed Technology

Embodiments of the disclosed technology use associated particle imaging ("API"). In general, API involves "tagging" a neutron emission in time, direction, or both time and direction by detecting a particle that is associated with the creation of a neutron. For example, embodiments of the disclosed technology use a deuterium-tritium generator as a neutron source. The deuterium-tritium generator produces monoenergetic neutrons (sometimes designated herein as "n" particles) and alpha particles (sometimes designated herein as "$^4$He" or "$\alpha$" particles) that travel in nearly opposite directions from one another. By detecting the arrival of an alpha particle and its position (e.g., in two dimensions) at an alpha particle detector located in a known geometry from the neutron source, the time and/or direction of the neutron emission can be determined. Although the direction of travel of the neutron is not exactly opposite of its associated alpha particle, the direction of travel is fixed and can be predicted accurately after account for the momentum of the particles in the deuterium beam. Accordingly, the direction of travel of the neutron can be determined accurately from the detected position of its associated alpha particle. In this way, the alpha particle can be used to "tag" the neutron emission. Further, because the time-of-flight of the neutron is fixed in a system that has a known geometry and that produces monoenergetic neutrons, a neutron detected at an array of neutron detectors positioned distally from the neutron source can be positively identified as the "tagged" neutron if it arrives in the expected time window and at an expected position at the detectors.

Furthermore, and as more fully explained below, embodiments of the disclosed technology use a transmission imaging approach. In particular, images of an interrogated object are generated based on the number of detected neutrons that are transmitted through the interrogated object without scattering or fissioning with nuclei in the interrogated object. The resulting images can be generated, for example, by normalizing the detected image results relative to a normalized image produced by the system when no object is present in the system.

The combination of API with transmission imaging is sometimes referred to herein as associated particle neutron radiography ("APNR"). Embodiments of the APNR systems described herein have a number of possible advantages over conventional neutron radiography systems. For example, the use of time and direction tagging allows embodiments of the APNR system to effectively remove measurement noise resulting from scattered neutrons (this technique is sometimes referred to as "electronic collimation"). The elimination of scattered neutrons enables high-contrast images, even through thick objects (e.g., large cargo containers), without the need for any physical collimation or shaping of the neutron beam. Thus, embodiments of the APNR system can be free of a physical collimator. The elimination of the need for physical collimation also enables wide cone-beam imaging without compromising image contrast. With wide cone-beam imaging, two-dimensional arrays of neutron detectors can be used, thus allowing the system to detect and use many more neutrons during the imaging process than is possible with conventional fan-based imaging. This ability to collect data in two dimensions also compensates for any loss in imaging capability that results from using an associated particle imaging technique. Additionally, wide cone-beam imaging and the absence of a physical collimator also enables the neutron source to be positioned close to the interrogated object, resulting in a compact geometry that requires less shielding overall. The overall footprint for embodiments of the APNR system can therefore be much smaller and lighter than conventional systems. Furthermore, APNR allows multiple neutron sources to be used (e.g., to be used simultaneously) during the neutron interrogation and image generation process. Consequently, multiple projection images from different angles can be generated simultaneously, significantly accelerating the image capture and reconstruction process (e.g., using computed tomography techniques, such as a filtered back projection technique).

FIG. 1 is a schematic block diagram of an exemplary APNR configuration 100 that can be used in embodiments of the disclosed technology. In general, the configuration 100 illustrates the basic components used to perform APNR using a single neutron source. As more fully discussed below, additional neutron sources are used in embodiments of the disclosed technology. For clarity, however, the one or more additional neutron sources are not shown in FIG. 1, though are understood to be present.

In FIG. 1, a neutron source 110 generates neutrons that interrogate an object 150 and that are detected by an array of neutron detectors 140. In the illustrated embodiment, the neutron source 110 is a portable deuterium-tritium ("DT") generator. In other embodiments, however, other neutron sources are used (e.g., other monoenergetic neutron generators, such as a deuterium-deuterium generator, a Californium neutron source, or any other neutron source). The DT generator illustrated in FIG. 1 includes a deuterium accelerator 112 that produces a deuterium beam that strikes a tritium-impregnated target 114 at a fixed location in the generator. In other embodiments, however, a tritium beam can strike a deuterium-impregnated target, or a mixed deuterium-tritium beam can strike a mixed deuterium-tritium target. The resulting interaction in the illustrated embodiment produces a monoenergetic neutron (e.g., a 14.1 MeV neutron) and an alpha particle (e.g., a 3.5 MeV alpha particle):

$$d+t \rightarrow n+{}^4He. \tag{1}$$

In the illustrated configuration, the deuterium accelerator 112 and the tritium-impregnated target 114 are located in fixed positions inside a sealed tube 116. With this configuration, the source of the neutrons can be considered to be the location of the tritium-impregnated target 114 that interacts with the deuterium beam. In certain embodiments, for instance, the size of the target (and thus the size of the source) is reduced or minimized so that the paths of the generated neutrons can be determined with higher accuracy. Also, because of the penetrating power of neutrons, the sealed tube 116 need not have any physical window or other aperture for emitting the neutrons. In the illustrated embodiment, the neutron emissions from the neutron source 110 are roughly isotropic.

The configuration 100 further includes an alpha particle detector 120. In the illustrated embodiments, the alpha particle detector 120 comprises one or more scintillators 122 that are coupled to one or more position-sensitive photomultiplier tubes 124. For example, in one embodiment, the scintillator 122 comprises one or more YAP scintillators positioned inside the sealed tube 116, and the photo-multiplier tube 124 comprises one or more fast, position-sensitive photomultiplier tubes positioned outside the sealed tube 116. In other embodiments, however, other scintillators or detection devices are used (e.g., zinc-oxide scintillators, fast inorganic scintillators, solid-state detectors, or one or more other suitable position-sensitive detector).

The configuration 100 additionally comprises an array of neutron detectors 140 positioned distally from the neutron source 110. In the illustrated embodiment, the neutron detectors comprise position-sensitive two-dimensional neutron "block detectors." Each neutron block detector can comprise any number of detectors in any arrangement (e.g., 10×10 arrays). The illustrated detectors are coupled to a plurality of photomultiplier tubes whose shared response can be used to determine the position on the array where the neutron interaction actually occurred. In other embodiments, other suitable neutron detectors are used (e.g., plastic scintillators, proton recoil scintillators, or other such fast neutron detectors). Furthermore, the timing resolution of the detectors is desirably high (e.g., a rise and decay time of 10 ns or less, 3 ns or less, or 1 ns or less) in order to improve the ability of the neutron detector to discriminate between neutrons generated at different times. The illustrated array of neutron detectors 140 can be used to determine the position of the detected neutron relative to the neutron source 120, as well as the time of flight of a neutron emitted from the neutron source 110. An interrogation region 160 in which an interrogated object 150 is positioned is located between the array of neutron detectors 140 and the neutron source 110.

The array of neutron detectors 140 and the alpha-particle detector 120 also help define the shape and size of the neutron beam emitted from the neutron source 110 that is used for neutron imaging. Although neutrons are emitted from the neutron source roughly isotropically, only a fraction of the emitted neutrons are useful for imaging purposes. In particular, the neutrons that are useful for imaging purposes comprise those neutrons that can be detected by the neutron detector 140 and whose associated alpha particles can be detected by the alpha-particle detector 120. The three-dimensional space traversed by these neutrons is referred to herein as the neutron beam, and typically forms a cone beam (e.g., cone beam 180) since the shape of the alpha-particle detector 120 is usually circular. Other beam shapes are possible, however, depending on the particular shape and configuration of the neutron detectors 140 and the alpha-particle detector 120.

To illustrate the principles of the APNR method, FIG. 1 further illustrates two possible neutron paths. A first neutron path 130 travels through the interrogated object 150 and is detected at position 142 on the face of the array of neutron detectors 140. A second neutron path 132 also travels through the interrogated object 150 but is scattered or otherwise interacts in the object 150. The resulting scattered or fission neutron arrives at a position 144 on the array of neutron detectors 140. Because the scattered or fission neutron does not arrive at the correct time and/or position on the neutron detector, the scattered or fission neutron detected at position 144 can be ignored for purposes of creating a projection image of the interrogated object 150.

The configuration 100 further comprises an image processing system 170 coupled to the neutron detector 140 and the alpha particle detector 120. In certain embodiments, the image processing system 170 comprises a computer-based system that executes image processing software. The image processing software can comprise, for example, computer-executable instructions stored on one or more non-transitory computer-readable media which when executed by a computer cause the computer to perform an image processing method (e.g., any of the image processing methods disclosed below). Exemplary computing environment for executing such computer-executable instructions are introduced below in Section IV.

Figure 2:
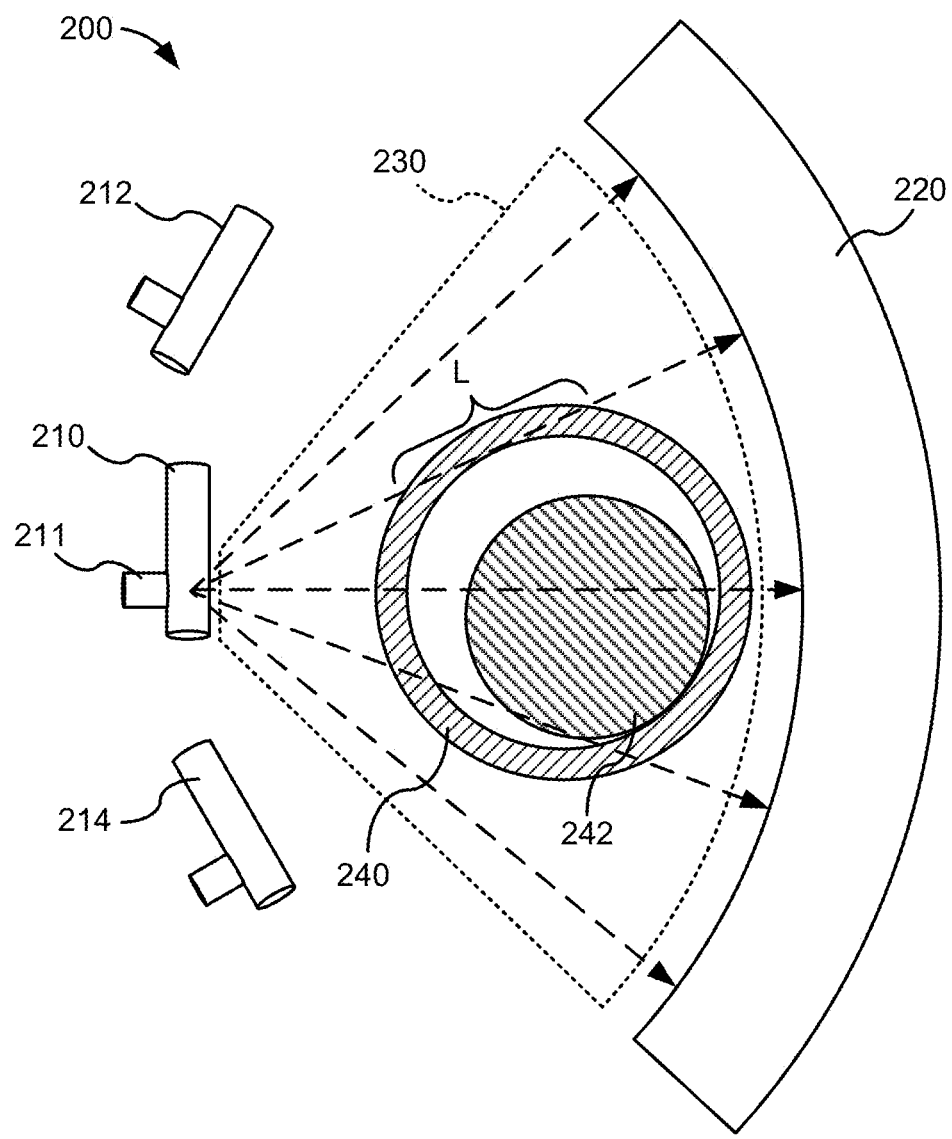
FIG. 2 is a schematic block diagram of a second APNR system according to another embodiment of the disclosed technology.

FIGS. 2-10 illustrate an exemplary image processing method that can be performed by the image processing system 170. FIGS. 2-10 also show exemplary images that can be obtained as a result of using embodiments of the disclosed technology. For illustrative purposes, the exemplary image processing method is described in relation to the configuration shown in FIG. 2. In particular, FIG. 2 shows an APNR configuration 200 comprising three neutron generators: a first neutron generator 210, a second neutron generator 212, and a third neutron generator 214. The following discussion focuses on the neutron generator 210 for illustration purposes. The neutron generator 210 comprises a DT generator and has an associated alpha particle detector 211 as described above with respect to FIG. 1. The APNR configuration further comprises a two-dimensional array of neutron detectors 220 configured to have a semi-spherical shape. The array of neutron detectors 220 is positioned distally from the neutron generator 210. An interrogation region 230 is defined between the neutron generator 210 and the array of neutron detectors 210. The semi-spherical shape of the neutron detector array 220 allows each individual neutron detector of the array 220 to be equidistant from the neutron source in the neutron generator 210. In other embodiments, the neutron detector array 220 is flat, partially spherical, or has some other shape. For example purposes, a lead pipe 240 that conceals a puck-shaped plastic object 242 is the object being interrogated in the interrogation region 230.

To implement the exemplary image processing method, certain baseline measurements and images can be determined. For example, in order to establish the expected time-of-flight of the neutrons emitted from the neutron source, counts at each of the neutron detectors on the array of neutron detectors 220 can be captured with respect to the time from detection of the associated alpha particle at the corresponding alpha detector pixel (e.g., the alpha detector pixel that indicates neutron emission in the direction of a particular neutron detector).

Figure 3:
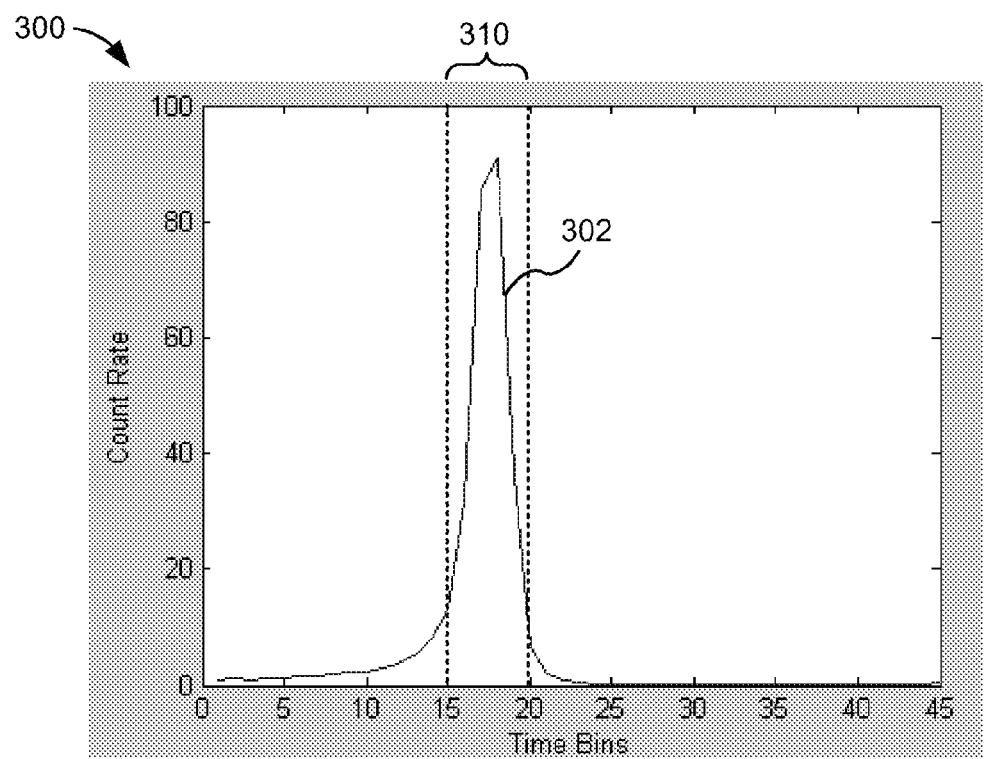
FIG. 3 is an image showing correlated results at a neutron detector from the APNR system of FIG. 2.

FIG. 3 is an image 300 showing a plot 302 from the results from one such neutron detector. For the neutron detector associated with image 300, the plot 302 shows that the normalized time-of-flight for a neutron is between about 15-20 nanoseconds from the time the associated alpha particle is detected at the corresponding alpha detector position. This information can be used to select the proper time period or time window (e.g., time window 310) in which to count a detected neutron as being the "tagged" neutron associated with a corresponding alpha particle detected at the alpha particle detector. The time window can comprise multiple time bins (or sampling periods) at which the neutron detectors operate. Further, the time window can have a variety of lengths relative to the observed peak. The size of the time window can depend, for example, on the overall path length, the types of materials to be interrogated, the number of sources being used in a particular configuration, or other such factors. For any given interrogation period, the counts that are observed as falling within the selected time window are collected and used to generate a projection image (sometimes referred to herein as a "projection").

The exemplary imaging process also uses a normalization image $I_0$. In particular embodiments, the normalization image $I_0$ is the image across one or more (e.g., all) of the neutron detectors of the neutron detector array 220 when no object is present in the interrogation region. The image $I_0$ can comprise, for example, the count rate of neutrons at each neutron detector across the neutron detector array 220 during the appropriate time window for tagged neutrons.

A projection image can then be taken with the object in the interrogation region 230. The image taken with the object in the interrogation region 230 results in a signal I for a given neutron detector in the array of neutron detectors:

$$I = I_0 e^{-\mu L} \quad (2)$$

where $I_0$ is the normalization image for the given neutron detector, $\mu$ is the attenuation coefficient for the object being interrogated, and L is the path length through the object.

If there are n multiple materials between the neutron source and the neutron detector, then the projection image observed is known to be a summation in the exponent:

$$I = I_0 e^{-\Sigma_{i=0}^{n} \mu_i L_i} \quad (3)$$

Consequently, the projection image of the object I can be normalized using the normalization image $I_0$, resulting in the summation of attenuations:

$$\log\left(\frac{I}{I_0}\right) = -\sum_{i=0}^{n} \mu_i L_i \quad (4)$$

Figure 4:
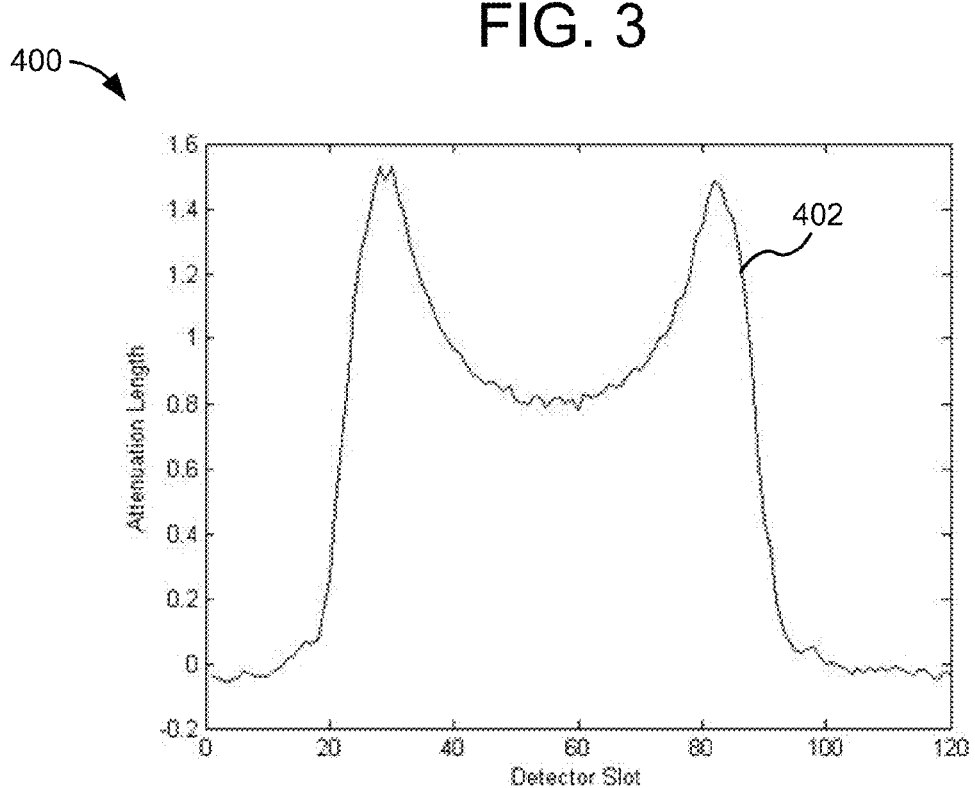
FIG. 4 is a normalized image from a row of neutron detectors of the APNR system of FIG. 2.

The attenuation lengths for each neutron detector in the neutron detector array can then be plotted together in order to form a two-dimensional projection image of the interrogated object. For example, FIG. 4 is an image 400 showing a plot 402 of attenuation lengths computed from a projection image of the lead pipe 240 and the plastic object 242 at one height of neutron detectors in the neutron detector array 220 of the APNR configuration 200.

If additional neutron sources are present (e.g., as with any of the multiple-neutron-source systems disclosed herein) or if the object is rotated or otherwise moved (or if the neutron generator and the array of neutron detectors are rotated or otherwise) to a new position, normalization images and projection images of the object can be taken at many different orientations around the object. From the resulting projection images, three-dimensional reconstructions can be performed to arrive at a complete three-dimensional image or representation of the interrogated object. For example, in particular embodiments, a filtered back projection technique is used to construct a three-dimensional image from the projection images from the multiple neutron sources as well as the images from different orientations of the multiple neutron sources. In other embodiments, maximum likelihood estimation maximization ("MLEM") techniques, ordered subset estimation maximization ("OSEM") techniques, or other iterative reconstruction techniques are used. The three-dimensional image or representation of the interrogated object can be displayed to a user of the system (e.g., on a suitable display device) and/or stored on computer-readable media (e.g., non-transitory computer-readable media).

Figure 5:
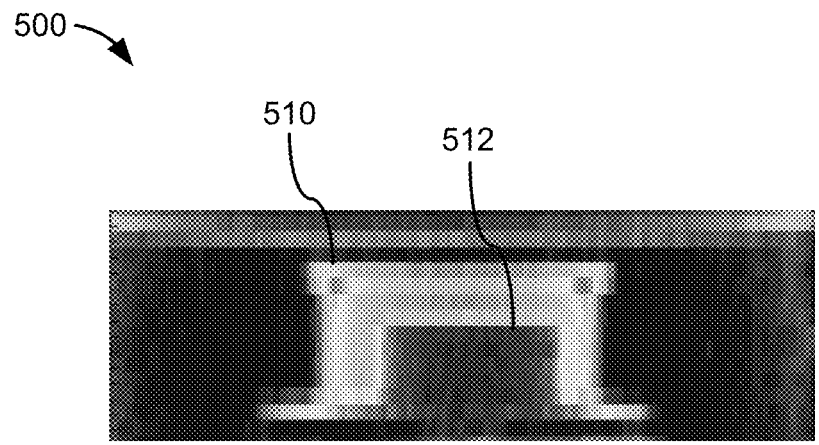
FIG. 5 is a two-dimensional projection image of an object illustrating an image that can be obtained from the APNR system of FIG. 2.

FIG. 5 is a two-dimensional projection image 500 of an object illustrating an image that can be obtained from the APNR system of FIG. 2. The image 500 is a side view of the lead pipe 240 and the plastic object 242 and clearly shows the lead pipe at region 510 and the plastic object at region 512. Image 500 also shows that the lead pipe and the plastic object can be differentiated from one another as a result of the neutron imaging technique.

Figure 6:
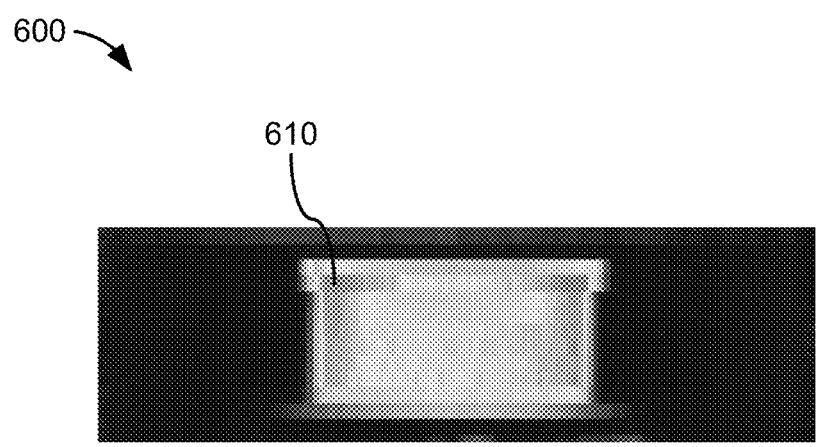
FIG. 6 is a two-dimensional projection image generated by an X-ray system showing the same object as in FIG. 5.

FIG. 6, by contrast, is a corresponding two-dimensional projection image 600 assembled from x-ray images of the lead pipe 510 and the plastic object 512. Image 600, however, only shows the lead pipe at region 610. The plastic object is not viewable at all in the image 600.

Figure 7:
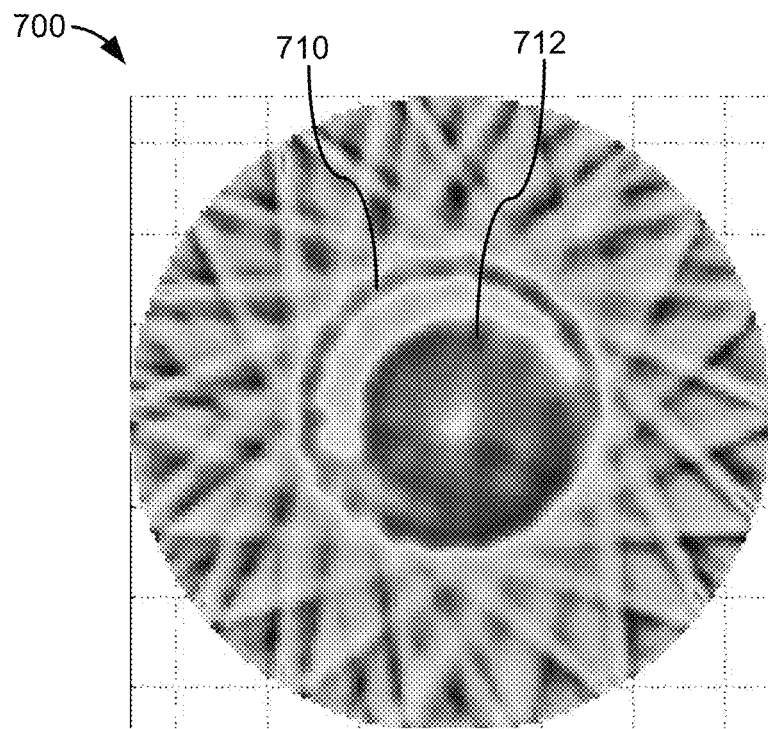
FIG. 7 is a slice through a reconstructed three-dimensional image of the object shown in FIG. 5. The image in FIG. 7 is generated from multiple projection images, such as projection images simultaneously obtained from the APNR system of FIG. 2.

FIG. 7 is an image 700 of a slice through a three-dimensional reconstruction assembled from multiple images. For example, the multiple images can be generated using simultaneously captured projection images from the multiple neutron sources in the APNR configuration 200. The image 700 is a slice through the lead pipe 240 and the plastic object 242. The image 700 is a slice that is generated from the planar images obtained from interrogating the sides of the objects using an appropriate three-dimensional reconstruction technique (e.g., a maximum likelihood estimation maximization ("MLEM"), ordered subset estimation maximization ("OSEM"), filtered back projection, or iterative reconstruction technique). The image 700 clearly shows the lead pipe at region 710 and the plastic object at region 712. Image 700 also shows that the lead pipe and the plastic object can be differentiated from one another as a result of the neutron imaging.

Figure 8:
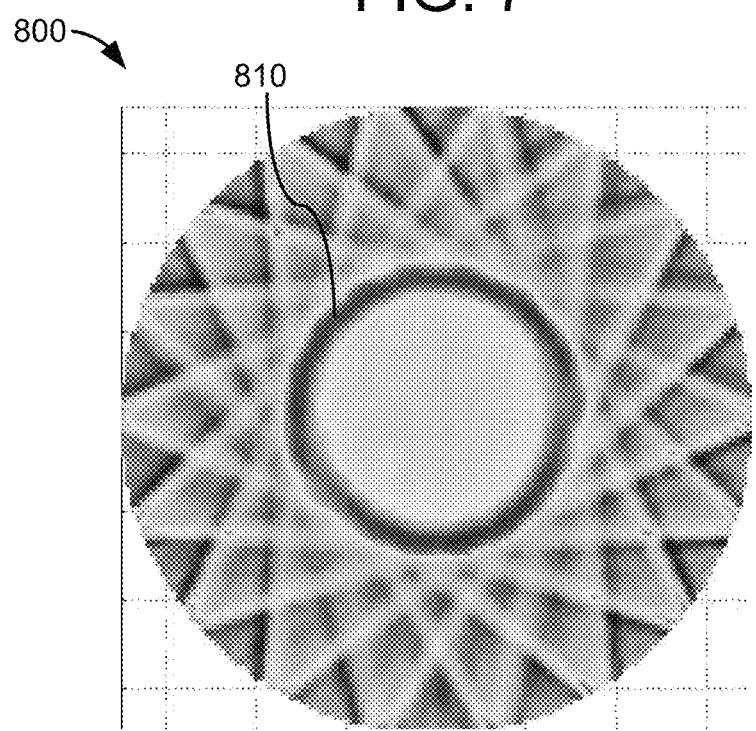
FIG. 8 is another image generated by an X-ray system showing the same object as in FIG. 8.

FIG. 8, by contrast, is a corresponding image 800 assembled from x-ray images of the lead pipe 510 and the plastic object 512. Image 800, however, only shows the lead pipe at 810. The plastic object is not visible at all in the image 800.

Figure 9:
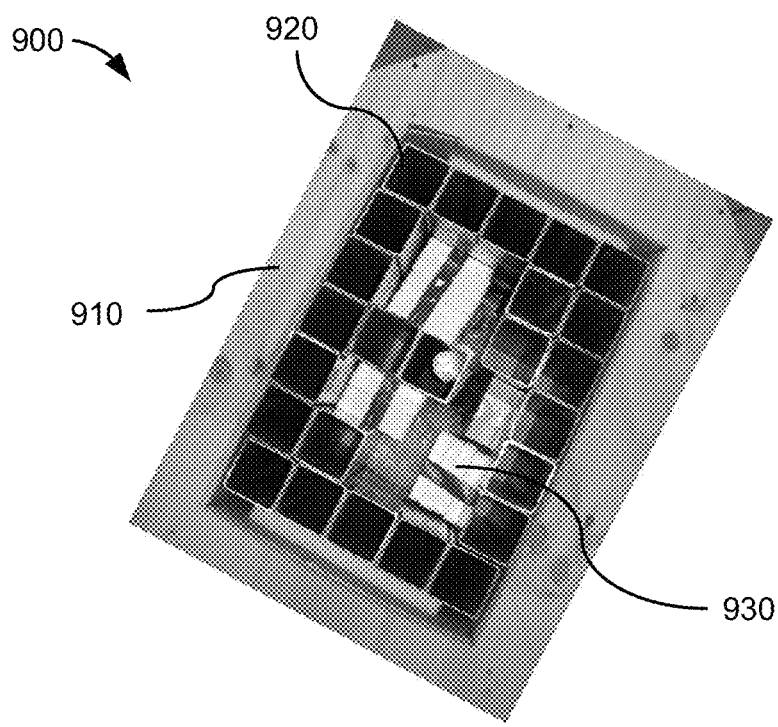
FIG. 9 is an optical image of a container comprising concealed objects.
Figure 10:
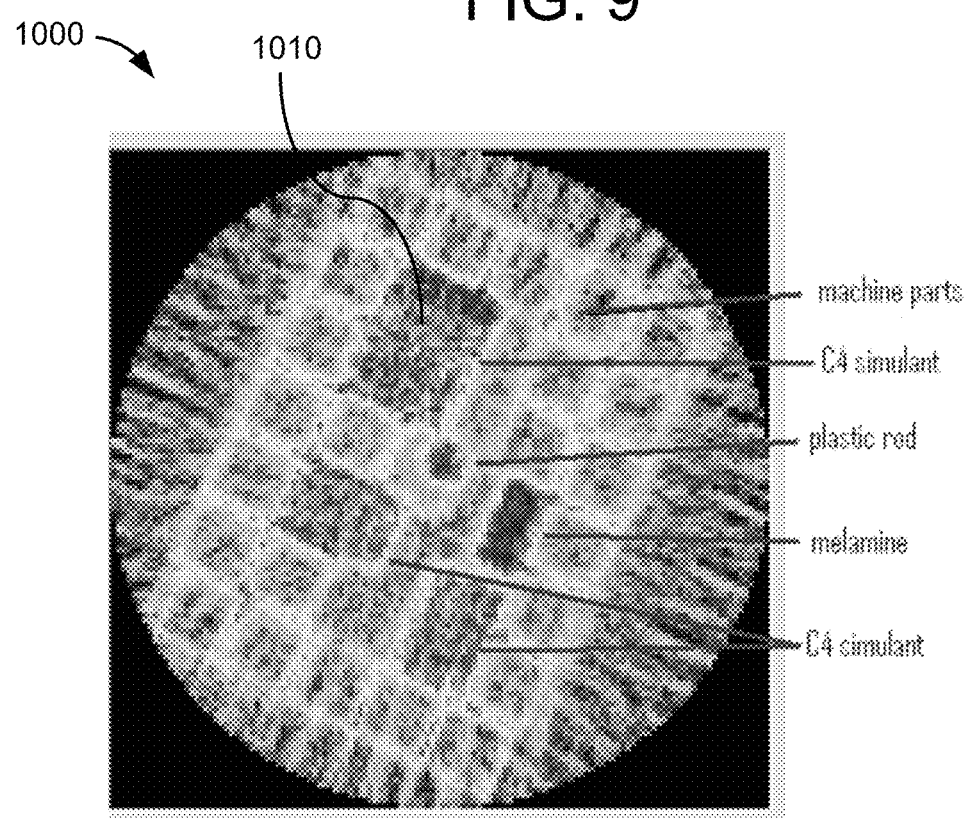
FIG. 10 is a reconstructed three-dimensional image of the container comprising the concealed object. The image in FIG. 10 can be generated from multiple projection images, such as projection images simultaneously obtained from any of the disclosed APNR systems.

FIGS. 9 and 10 illustrate another example of images that can be produced using embodiments of the disclosed technology. In particular, FIG. 9 is an optical image 900 of the top view of a cargo container 910. The image 900 shows that the cargo container 910 contains multiple square-shaped metal machine parts (one of which is shown as metal machine part 920) and concealed objects (one of which is shown as concealed object 930) located between some of the machine parts. In image 900, the concealed objects include objects that simulate the presence of illegal or dangerous materials, including a C4 simulant and melamine. In practice, however, embodiments of the disclosed technology can be used to detect actual illegal or dangerous materials.

FIG. 10 is an image 1000 of a slice through a three-dimensional reconstruction assembled from multiple images. For example, the multiple images can be generated using simultaneously captured projection images from the multiple neutron sources in the APNR configuration 200 or from the multiple neutron sources in any of the disclosed embodiments. The image 1000 is a slice through the cargo container 910 and clearly shows the concealed objects (one of which is shown as concealed object 1010). Image 1000 also shows that the concealed objects can be easily differentiated from the machine parts 920 as a result of the neutron imaging.

III. Exemplary Multiple Source Configurations

As explained above, three-dimensional image information can be generated from multiple projection images. By using the API technique together with transmission imaging of the transmitted neutrons, the APNR method allows multiple sources to be introduced into the system. The introduction of multiple sources can consequently allow projection images to be simultaneously (or at least partially simultaneously) generated, resulting in a significant increase in the speed with which three-dimensional information can be generated. These higher speeds make embodiments of the APNR system desirable for a wide variety of commercial uses. For example, embodiments of the multi-source APNR systems can be used to inspect shipping containers, trucking trailers, air cargo containers, or any other container or vessel in which objects can be contained or concealed. Embodiments of the disclosed technology can also be used to perform medical imaging.

The time and/or direction tagging capabilities of the APNR system allow multiple projections to be taken simultaneously (or substantially simultaneously) using more than one source because the neutrons being detected can be accurately tagged to their proper source. As long as there is a low probability of crosstalk, multiple projection images can be generated simultaneously with little loss of useful neutrons and little noise.

To appreciate the low probability of crosstalk in APNR systems configured according to the disclosed technology, consider the following example. First, assume that a neutron source produces $10^8$ neutrons per second over a sphere. Also assume that the timing resolution is 1 ns, that the detector array covers 0.0785% of the spherical surface (e.g., the detector array comprises one row of 1-inch-by-1-inch detectors, 6 feet long, positioned 7.6 feet from the source), and that the alpha-particle detector associated with the neutron source covers a solid angle equivalent to the neutron detector. Also assume that there is no shielding between the sources and the detector arrays. In this configuration, there are 0.1 neutrons on average from a source for each time bin, but the solid angle only captures 0.1×0.000785=0.0000785 neutrons per time bin. Thus, the probability that a neutron will arrive in a time bin from a single source is 0.0000785. With N sources, given that one source produced a neutron in a particular time bin, the probability that no others will be produced at the same time is $(1-0.0000785)^{N-1}$. With 1000 sources, for example, given that one source has produced a neutron in a time bin, the probability that another will collide with it is only 7.54%. For 100 sources, 0.77%, and for 10 sources 0.071%.

Furthermore, this exemplary calculation is based only on time tagging. If directional tagging is also included, then two neutrons arriving in the same time bin may still be separated through direction tagging, further reducing the neutron loss. Therefore, two or more multiple sources can be used to capture multiple projections at once with very little loss of neutrons. The number of sources can vary from implementation to implementation, but in certain implementations the number of sources is 100 neutron sources or fewer, 10 neutron sources or fewer, 4 neutron sources or fewer, or 2 neutron sources.

Figure 11:
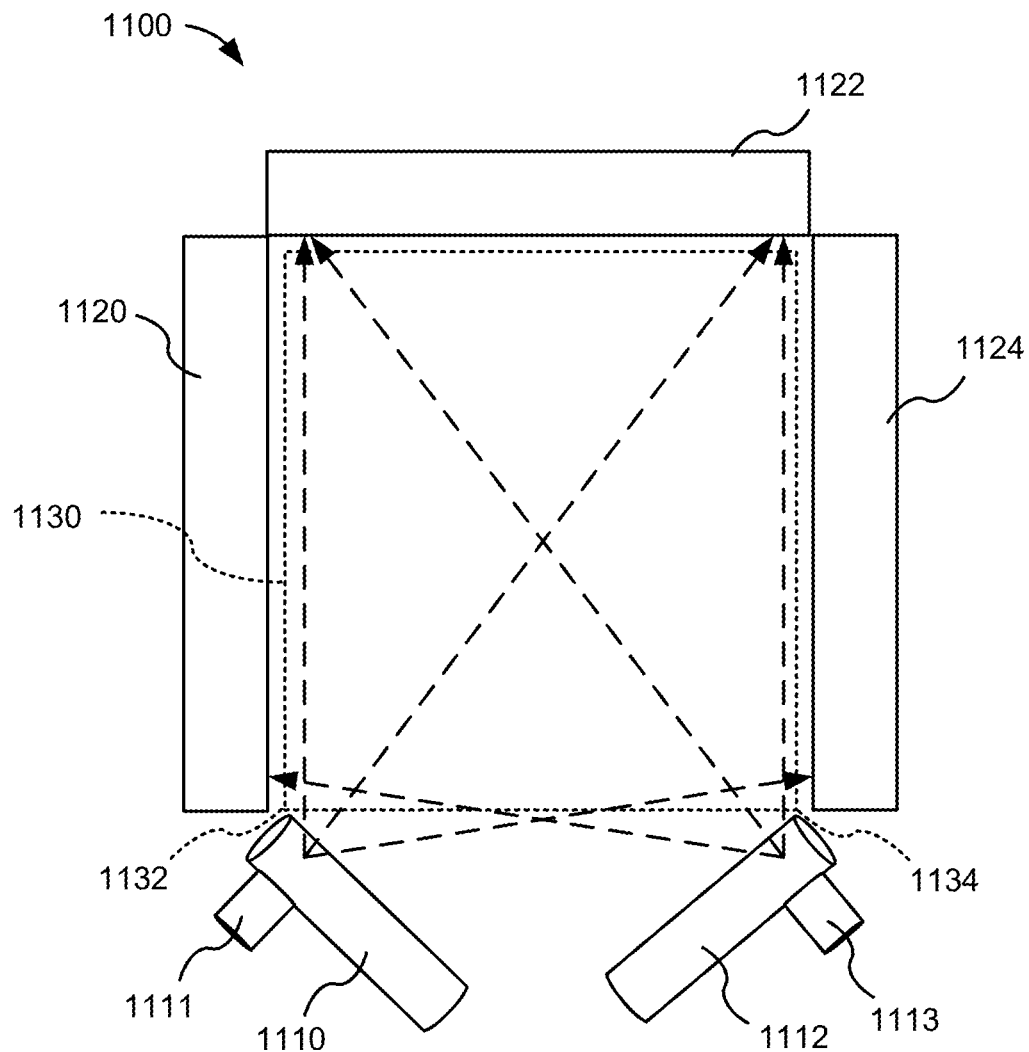
FIG. 11 is a schematic block diagram of a third APNR system having multiple neutron sources according to another embodiment of the disclosed technology.

FIG. 11 is a schematic block diagram illustrating an exemplary system 1100 having two neutron sources: a first neutron source 1110 and a second neutron source 1112. The first neutron source 1110 and the second neutron source 1112 can be any suitable neutron source (e.g., as described above with respect to FIG. 1). In the illustrated embodiment, for example, the neutron sources 1110, 1112 are DT neutron generators. The first neutron source 1110 is located near or adjacent to an associated alpha particle detector 1111, which can be any suitable alpha particle detector (e.g., as described above with respect to FIG. 1). In the illustrated embodiment, for example, the alpha particle detector 1111 is integrally coupled to the tube (which may or may not be shielded) in which the neutron source 1110 is located as in FIG. 1. In other embodiments, however, the alpha particle detector can be located in a different position or distance from the neutron source. Furthermore, the alpha particle detector can include multiple alpha particle detectors arranged two-dimensionally to provide a large area of alpha particle detection. The alpha particle detector 1111 is configured to detect a position, time, or both position and time of an alpha particle emitted by the first neutron source 1110 during neutron generation. The second neutron source 1112 is also located near or adjacent an associated alpha particle detector 1113, which can be configured as described above with respect to alpha particle detector 1111.

The system 1100 further comprises three planar arrays of neutron detectors 1120, 1122, 1124. In the illustrated embodiment, the three planar arrays of neutron detectors 1120, 1122, 1124 are arranged along each of the edges of a square or rectangular interrogation area 1130. The interrogation area 1130 can be designed to hold an object of a particular size and configuration. For example, the interrogation area 1130 can be designed so that a standardized cargo container (e.g., an airline cargo container, a shipping container, or any other container) can fit within the interrogation area 1130 and so that the edges of the cargo container are near the neutron sources 1110, 1112 and the front faces of the three arrays of neutron detectors 1120, 1122, 1124 (e.g., within 3 feet or less, within 1 foot or less, or any other short distance).

Each of the arrays of neutron detectors can comprise neutron detectors arranged rectilinearly (or at least partially rectilinearly) into rows and column, thereby forming a two-dimensional array. It should be understood, however, that reference to a row or a column does not require the neutron detectors to be aligned horizontally or vertically, respectively. Instead, neutron detectors in a row can be aligned on an axis angularly translated from the horizontal axis (for example, by as much 90 degrees) and neutron detectors in a column can be aligned on an axis angularly translated from the vertical axis (for example, by as much 90 degrees). The neutron detectors on an array of neutron detectors can also be arranged in other regular or irregular configurations (e.g., circular or partially circular, more densely packed in the center of the array, or other such configurations). Furthermore, although the arrays of neutron detectors 1120, 1122, 1124 are shown as planar arrays, the arrays can have some radius of curvature. Additionally, instead of being arranged in a 2-dimensional array, the neutron detectors can be arranged in a single row or column (e.g., forming a single horizontal or vertical detection area).

In general, the neutron detectors on each of the planar arrays 1120, 1122, 1124 in the illustrated embodiment are desirably arranged to form a two-dimensional target that is configured to detect a large fraction of the neutrons emitted from the neutron sources, thus creating a wide field of view for the system. As noted above, this wide field of view is possible because the neutron sources 1110, 1112 do not need a physical collimator and have wide cone-beam angles. The absence of the physical collimator also allows the neutron sources to be placed closer to the interrogation area 1130. For example, in the illustrated embodiment, the first neutron source 1110 is located adjacent to a first corner 1132 of the interrogation area 1130, and the neutron source 1112 is located adjacent to a second corner 1134 of the interrogation area 1130. Furthermore, the neutron sources 1110, 1112 are oriented at 45° angles relative to the corners 1132, 1134 of the interrogation area 1130 so that the wide-angle neutron cone beams emitted from the neutron sources 1110, 1112 cover all or substantially all of the interrogation area 1130. This wide-angle coverage is illustrated by the dashed lines ending in arrows, which illustrate exemplary neutron beam paths. The orientation of the neutron sources 1110, 1112 can vary from embodiment to embodiment (e.g., between 40° and 50° relative to an adjacent edge of the interrogation region, between 30° and 60° relative to an adjacent edge of the interrogation region, or any other orientation angle). Furthermore, in the illustrated embodiment, the cone-beam angle of each of the neutron sources 1110, 1112 is about 90°. The cone-beam angle of the neutron sources 1110, 1112, however, can vary from implementation to implementation (e.g., any cone-beam angle of 180° or less).

Although only two neutron sources 1110, 1112 are shown in FIG. 11, one or more additional neutron sources can be implemented with the system 1100. The one or more additional neutron sources can be positioned at a variety of different positions around the interrogation area 1130 (e.g., adjacent to the opposite corners of the interrogation area 1130, along any of the edges of the interrogation area 1130, at any position above or below the interrogation area 1130 or at any other suitable position).

Furthermore, the interrogation area 1130 or any one or more of the neutron sources 1110, 1112 and arrays of neutron detectors 1120, 1122, 1124 can be movable or rotatable relative to one another in order to obtain additional projection images. For example, the interrogation area 1130 can be rotatable. The system 1100 can also be configured to allow for translation or rotation in any dimension of any one or more of the interrogation area 1130, the neutron sources 1110, 1112, or the arrays of neutron detectors 1120, 1122, 1124. For example, if the neutron detectors on the arrays of neutron detectors 1120, 1122, 1124 are aligned in a single row or column, any of the interrogation area, arrays 1120, 1122, 1124, or neutron sources 1110, 1112 can be moved so that an object in the interrogation region is scanned at multiple positions, thereby producing multiple 1-dimensional images that permit reconstruction into a three-dimensional image.

An image processing system (not shown) can also be implemented as part of the system 1100. For example, an image processing system as described above can be coupled to the alpha particle detectors 1111, 1113, and to the arrays of neutron detectors 1120, 1122, 1124. The image processing system can be configured to reconstruct three-dimensional images using any of the disclosed image processing methods. The use of multiple non-collimated neutron sources, together with the ability to tag the neutron in time and/or direction, allows a three-dimensional image of the interrogated area to be generated in less time than in conventional systems. For example, for the illustrated system 1100 having two neutron sources 1110, 1112, reconstructed images can be generated approximately twice as quickly as conventional single source systems. Furthermore, and as explained above, the ability to tag the neutrons in time and with a high time resolution allows the system to differentiate the source of the detected neutrons with high accuracy and with very little loss of data due to crosstalk. If two neutrons are detected at the arrays of neutron detectors during the same time bin, directional tagging allows for the separation of these two events such that each neutron can be assigned to the correct source. Accordingly, the neutron sources 1110, 1112 can be operated simultaneously during the neutron interrogation process. Furthermore, the system 1100 can distinguish between multiple sources during the neutron interrogation process when two (or more) neutrons are detected in the same time bin so long as the neutrons are detected at different positions on the arrays of neutron detectors.

Figure 12:
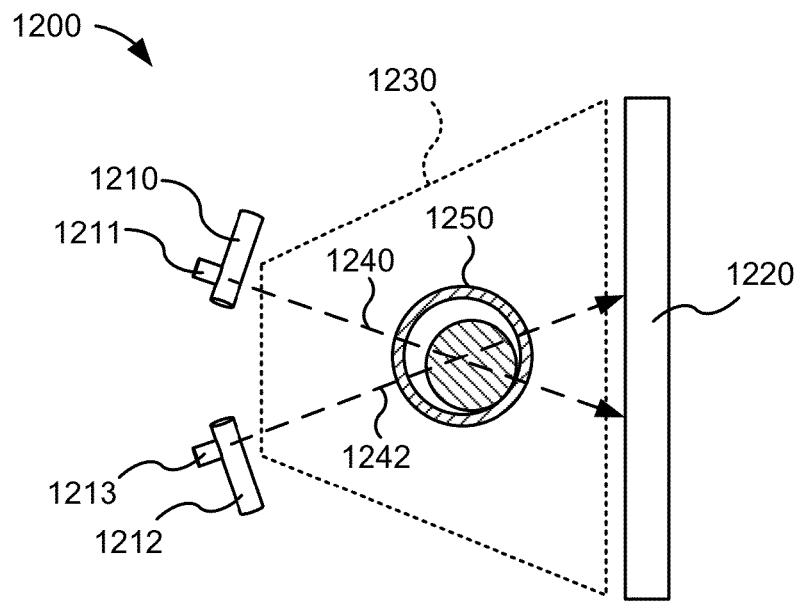
FIG. 12 is a schematic block diagram of a fourth APNR system having multiple neutron sources according to another embodiment of the disclosed technology.

FIG. 12 is a schematic block diagram illustrating an exemplary system 1200 having a single array of neutron detectors 1220 and two neutron sources: a first neutron source 1210 and a second neutron source 1212. As above, the first neutron source 1210 and the second neutron source 1212 can be any suitable neutron source. In the illustrated embodiment, a first alpha particle detector 1211 is associated with the first neutron source and a second alpha particle detector 1213 is associated with the second neutron source 1212. As above, the alpha particle detectors 1211, 1213 are configured to detect a position, time, or both position and time of an alpha particle emitted by their respective associated neutron sources 1210, 1212 during neutron generation.

In contrast to the system 1100, the system 1200 comprises a single array of neutron detectors 1220 positioned distally from the neutron sources 1210, 1212. The array of neutron detectors 1220 can have any of the configurations or arrangements discussed above with respect to system 1100. The space between the array of neutron detectors 1220 and the neutron sources 1210, 1212 defines an interrogation area 1230 in which one or more objects (e.g., object 1250) can be positioned and interrogated using the system 1200. As with system 1100, the interrogation area 1230 can be designed to hold an object of a particular size and configuration.

In general, the neutron detectors on the array 1220 are desirably arranged to form a two-dimensional target that is configured to detect a large fraction of neutrons emitted from the neutron sources 1210, 1212, thus creating a wide field of view. In the illustrated embodiment, the neutron sources 1210, 1212 are positioned apart from one another by a distance that is approximately half the length of the face of the array of neutron detectors. This distance can vary from implementation to implementation. For example, the neutron sources 1210, 1212 can be placed at a distance from one another that is the same or substantially the same (e.g., within 10%) of the length of the face of the array of neutron detectors 1220, or at a larger or smaller distance. Furthermore, the illustrated neutron sources 1210, 1212 are oriented at angles relative to the normal of the face of the array of neutron detectors 1220. These orientation angles can vary from implementation to implementation. For example, the orientation angles can be selected based in part on the cone-beam angles of the neutron detectors 1210, 1212 and so that the number of neutrons detected at the array of neutron detectors 1220 is increased (e.g., maximized). As with the system 1100, the cone-beam angles of the neutron sources 1210, 1212 can vary from implementation to implementation.

Although only two neutron sources 1210, 1212 are shown in FIG. 12, one or more additional neutron sources can be implemented with the system 1200. Furthermore, the one or more additional neutron sources can be positioned at a variety of different positions around the interrogation area 1230 (e.g., along a hemisphere, square, or other regular or irregular shape surrounding the interrogation area 1230, at any position above or below the interrogation area 1230, or at any other position).

Furthermore, and in manners similar to those described above with respect to system 1100, any one or more of the interrogation area 1230, the arrangement of neutron sources 1210, 1212, or the array of neutron detectors 1220 can be movable or rotatable relative to one another in order to obtain additional projection images.

An image processing system (not shown) can also be implemented as part of the system 1200. For example, an image processing system as described above can be coupled to the alpha particle detectors 1211, 1213, and to the arrays of neutron detectors 1220. The image processing system can be configured to reconstruct three-dimensional images using any of the disclosed image processing methods. The ability to tag neutrons in time with a high time resolution allows the system to differentiate the source of the detected neutrons with high accuracy and with very little loss of data due to crosstalk. Furthermore, if two neutrons are detected by the array of neutron detectors 1220 during the same time bin, directional tagging can be used to separate the two events so that each neutron can be assigned to the correct source. For example, neutron paths 1240, 1242 can be differentiated from one another if they are detected during the same time bin by using directional tagging. The neutron sources 1210, 1212 can therefore be operated simultaneously during the neutron interrogation process. Furthermore, embodiments of the system 1200 can distinguish between multiple sources during the neutron interrogation process when two (or more) neutrons are detected in the same time bin (or time window) so long as the neutrons are detected at different positions on the array of neutron detectors.

Figure 13:
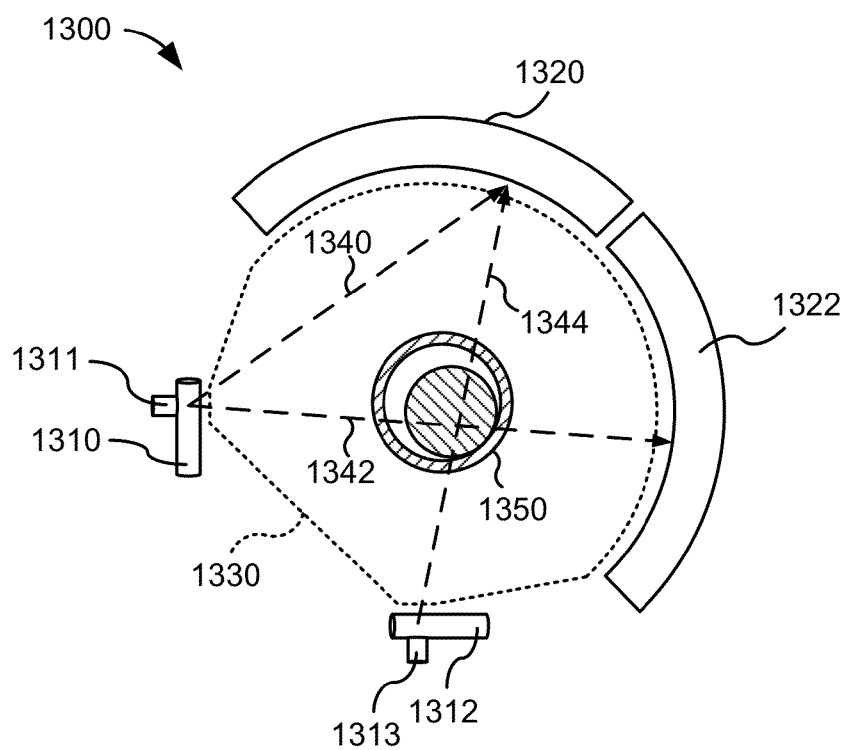
FIG. 13 is a schematic block diagram of a fifth APNR system having multiple neutron sources according to another embodiment of the disclosed technology.

FIG. 13 is a schematic block diagram illustrating an exemplary system 1300 comprising two neutron sources: a first neutron source 1310 and a second neutron source 1312. As above, the first neutron source 1310 and the second neutron source 1312 can be any suitable neutron source. In the illustrated embodiment, a first alpha particle detector 1311 is associated with the first neutron source 1310 and a second alpha particle detector 1313 is associated with the second neutron source 1312. As above, the alpha particle detectors 1311, 1313 are configured to detect a position, time, or both position and time of an alpha particle emitted by their respective associated neutron sources 1310, 1312 during neutron generation.

In contrast to the system 1200, the system 1300 comprises two arrays of neutron detectors: a first array of neutron detectors 1320, and a second array of neutron detectors 1322. Further, the arrays of neutron detectors 1320, 1322 are curved or arched so as to have a semi-cylindrical or semi-spherical shape. The radii of curvature of the arrays of the neutron detectors 1320, 1322 can be selected so that the distance between a respective neutron source and its oppositely positioned array of neutron detectors is constant or nearly constant across all neutron detectors of the respective array. Alternatively, the arrays of the neutron detectors 1320, 1322 can have other radii of curvature. The neutron detectors on the arrays of neutron detectors 1320, 1322 can be positioned in any arrangement or configuration discussed above with respect to system 1100.

The space between the arrays of neutron detectors 1320, 1322 and the neutron sources 1310, 1312 defines an interrogation area 1330 in which one or more objects (e.g., object 1350) can be positioned and interrogated using the system 1300. As with system 1300, the interrogation area 1330 can be designed to hold an object of a particular size and configuration.

In general, the neutron detectors on the arrays 1320, 1322 are desirably arranged to form a two-dimensional target that is configured to detect a large fraction of neutrons emitted from the neutron sources 1310, 1312, thus creating a wide field of view. Furthermore, in the illustrated embodiment, the arrays of neutron detectors 1320, 1322 are positioned and oriented so that they each face a respective one of the neutron sources 1310, 1312 but can still detect neutrons from both of the neutron sources 1310, 1312. In the illustrated embodiment, the neutron sources 1310, 1312 are positioned apart from one another so that the first neutron source 1310 is facing a front of the object 1350, whereas the second neutron source 1312 is facing a side of the object 1350 (e.g., a side facing 90° from the front). Furthermore, the neutron sources 1310, 1312 are oriented at different angles from each other. For example, in the illustrated embodiment, the neutron sources 1310, 1312 are oriented at 90° angles from one another. This orientation and positioning allows the system 1300 to generate projection images of different sides of the object simultaneously. Such different projection images are highly useful in constructing a meaningful three-dimensional image using a small number of projection images. The positions and orientation of the neutron sources in the system 1300 should not be construed as limiting, however, as the positions and orientations can vary from implementation to implementation. For example, the positions and orientation angles can be selected based in part on the cone-beam angles of the neutron sources 1310, 1312 and so that the number of neutrons detected at the arrays of neutron detectors 1320, 1322 is increased (e.g., maximized). As with the system 1100, the cone-beam angles of the neutron sources 1310, 1312 can vary from implementation to implementation.

Although only two neutron sources 1310, 1312 are shown in FIG. 13, one or more additional neutron sources can be implemented with the system 1300. Furthermore, the one or more additional neutron sources can be positioned at a variety of different positions around the interrogation area 1330 (e.g., along a hemisphere, square, or other regular or irregular shape surrounding the interrogation area 1330, at any position above or below the interrogation area 1330, or at any other position).

Additionally, and in manners similar to those described above with respect to system 1100, any one or more of the interrogation area 1330, the arrangement of neutron sources 1310, 1312, or the arrays of neutron detectors 1320, 1322 can be movable or rotatable relative to one another in order to obtain additional projection images.

An image processing system (not shown) can also be implemented as part of the system 1300. For example, an image processing system as described above can be coupled to the alpha particle detectors 1311, 1313, and to the arrays of neutron detectors 1320, 1322. The image processing system can be configured to reconstruct three-dimensional images using any of the disclosed image processing methods. The ability to tag neutrons in time with a high time resolution allows the system to differentiate the source of the detected neutrons with high accuracy and with very little loss of data due to crosstalk. Furthermore, if two neutrons are detected by the arrays of neutron detectors 1320, 1322 during the same time bin, directional tagging can be used to separate the two events so that each neutron can be assigned to the correct source. For example, neutron path 1342 and neutron path 1344 can be differentiated from one another if they are detected during the same time bin by using directional tagging. However, in embodiments of the disclosed technology, neutron path 1340 and neutron path 1344 cannot be differentiated from one another if they are detected during the same time bin because the neutron paths 1340, 1344 are detected at the same position on the array of neutron detectors 1320. Consequently, directional tagging will not be able to resolve the paths because both paths will be predicted as arriving at the same position. In this event, the data from detecting the neutrons on the neutron paths 1340, 1344 is not used in image generation. Nonetheless, this event is extremely rare and does not significantly impact the overall speed with which the system 1300 can be operated. Thus, by using a system such as system 1300, the neutron sources 1310, 1312 can be operated simultaneously during the neutron interrogation process. Furthermore, embodiments of the system 1300 can distinguish between multiple sources during the neutron interrogation process when two (or more) neutrons are detected in the same time bin so long as the neutrons are detected at different positions on the arrays of neutron detectors.

Figure 14:
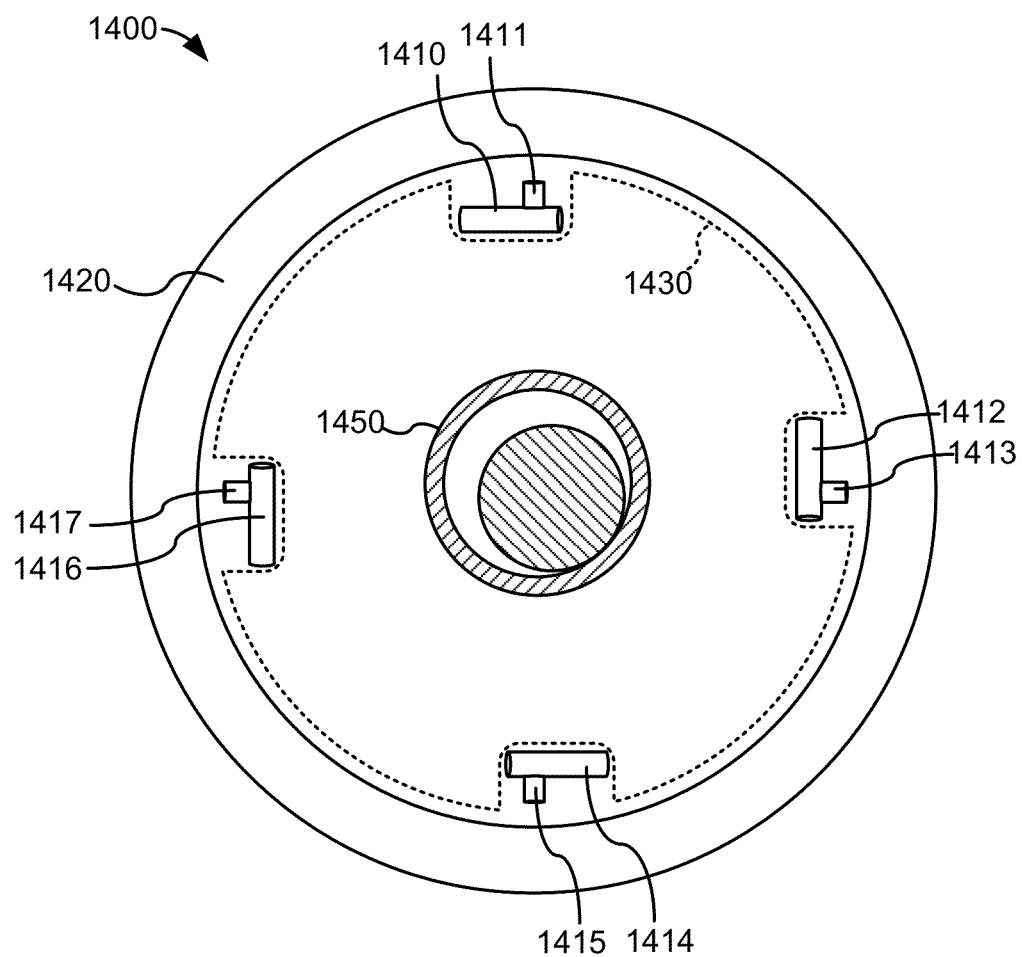
FIG. 14 is a schematic block diagram of a sixth APNR system having multiple neutron sources according to another embodiment of the disclosed technology.

FIG. 14 is a schematic block diagram illustrating a top view of an exemplary system 1400 comprising four neutron sources: a first neutron source 1410, a second neutron source 1412, a third neutron source 1414, and a fourth neutron source 1416. As above, the neutron sources 1410, 1412, 1414, 1416 can be any suitable neutron source. In the illustrated embodiment, a first alpha particle detector 1411 is associated with the first neutron source 1410, a second alpha particle detector 1413 is associated with the second neutron source 1412, a third alpha particle detector 1415 is associated with the third neutron source 1414, and a fourth alpha particle detector 1417 is associated with the fourth neutron source 1416. As above, the alpha particle detectors 1411, 1413, 1415, 1417 can be configured to detect position, time, or both position and time of an alpha particle emitted by their respective associated neutron sources 1410, 1412, 1414, 1416 during neutron generation.

In contrast to the system 1300, the system 1400 comprises a ring-shaped array of neutron detectors 1420. Furthermore, the neutron sources 1410, 1412, 1414, 1416 are positioned in the interior of the ring-shaped array 1420. The radius of the ring-shaped array 1420 can be selected so that the system 1400 is large enough to enclose the neutron sources 1410, 1412, 1414, 1416 and the desired object to be interrogated. Additionally, although FIG. 14 shows the ring-shaped array of neutron detectors 1420 as being a contiguous, integrated ring, the ring-shaped array can comprise multiple separate arrays (e.g., segments) of neutron detectors positioned around the neutron sources 1410, 1412, 1414, 1416 in a generally ring shape (with or without gaps between each of the arrays). Furthermore, in certain embodiments, fewer or no neutron detectors are located in the areas behind the neutron sources 1410, 1412, 1414, 1416. The neutron detectors on the ring-shaped array of neutron detectors 1420 can be positioned in any arrangement or configuration along the ring as discussed above with respect to system 1100.

The majority of the interior of the ring-shaped array of neutron detectors 1420 defines an interrogation area 1430 in which one or more objects (e.g., object 1450) can be positioned and interrogated using the system 1400. As with system 1100, the interrogation area 1430 can be designed to hold an object of a particular size and configuration.

In general, the neutron detectors on the ring-shaped array 1420 are desirably arranged to form a two-dimensional target that detects a large fraction of neutrons emitted from the neutron sources 1410, 1412, 1414, 1416, thus creating a wide field of view. In the illustrated embodiment, the neutron sources 1410, 1412, 1414, 1416 are positioned apart from one another so that each of the neutron sources faces a different side of the object 1450 (e.g., sides that face 90° from each other). Furthermore, the neutron sources 1410, 1412, 1414, 1416 are oriented at different angles from each other. For example, in the illustrated embodiment, the neutron sources 1410, 1412, 1414, 1416 are oriented at 90° angles from one another, though other angles are also possible. This orientation and positioning allows the system 1400 to generate projection images of four sides of the object simultaneously. Such different projection images are highly useful in constructing a meaningful three-dimensional image using a small number of projection images. The positions and orientations of the neutron sources in the system 1400 should not be construed as limiting, as the positions and orientations can vary from implementation to implementation. For example, the positioning and orientation angles can be selected based in part on the cone-beam angle of the neutron sources 1410, 1412, 1414, 1416 so that the number of neutrons detected at the array of neutron detectors 1420 is increased (e.g., maximized). As with the system 1100, the cone-beam angles of the neutron sources 1410, 1412, 1414, 1416 can vary from implementation to implementation.

Although only four neutron sources 1410, 1412, 1414, 1416 are shown in FIG. 14, one or more additional neutron sources (or fewer neutron sources) can be implemented with the system 1400. Furthermore, the one or more additional neutron sources can be positioned at a variety of different positions in the interior of the ring-shaped array of neutron detectors 1420 or in the interrogation area 1430. For example, one or more additional neutron sources can be positioned between each pair of neutron sources 1410, 1412, 1414, 1416 along the perimeter of the interrogation region 1430 and oriented toward the center of the interrogation area 1430. In other embodiments, the sources can be placed on a plane parallel to the ring-shaped array of neutron detectors 1420 but not within the interior of the ring-shaped array. This configuration can help prevent imaging of the neutron sources themselves. Further, in this configuration, the neutron sources can be tilted toward the detector plane and the detectors tilted toward the source plane to improve neutron detection.

Moreover, and in manners similar to those described above with respect to system 1100, any one or more of the interrogation area 1430, the arrangement of neutron sources 1410, 1412, 1414, 1416, or the ring-shaped array of neutron detectors 1420 can be movable or rotatable relative to one another in order to obtain additional projection images. Furthermore, the system 1400 can be oriented vertically and included as part of an inspection system that includes a conveyor belt or other mechanism for moving the object to be interrogated through the system (e.g., system 1500 discussed below).

An image processing system (not shown) can also be implemented as part of the system 1400. For example, an image processing system as described above can be coupled to the alpha particle detectors 1411, 1413, 1415, 1417 and to the ring-shaped array of neutron detectors 1420. The image processing system can be configured to reconstruct three-dimensional images using any of the disclosed image processing methods. For the system 1400 (or any other system in which one or more of the neutron sources are positioned between a neutron detector and another neutron source), the neutron sources across from one another will be visible in the projection images taken. But the normalization image that is created for use in the image processing method (such as the image processing methods described above) will also contain the neutron sources. Therefore, the image of the other sources will be removed when the observed image is normalized during the image reconstruction process. The ability to tag neutrons in time with a high time resolution allows the system to differentiate the source of the detected neutrons with high accuracy and with very little loss of data due to crosstalk. Furthermore, if two (or more) neutrons are detected by the ring-shaped array of neutron detectors 1420 during the same time bin, directional tagging can be used to separate the two events so that each neutron can be assigned to the correct source. Thus, by using a system such as system 1400, the neutron sources 1410, 1412, 1414, 1416 can be operated simultaneously during the neutron interrogation process. Furthermore, embodiments of the system 1400 can distinguish between multiple sources during the neutron interrogation process when two (or more) neutrons are detected in the same time bin (or time window) so long as the neutrons are detected at different positions on the ring-shaped array.

Figure 15:
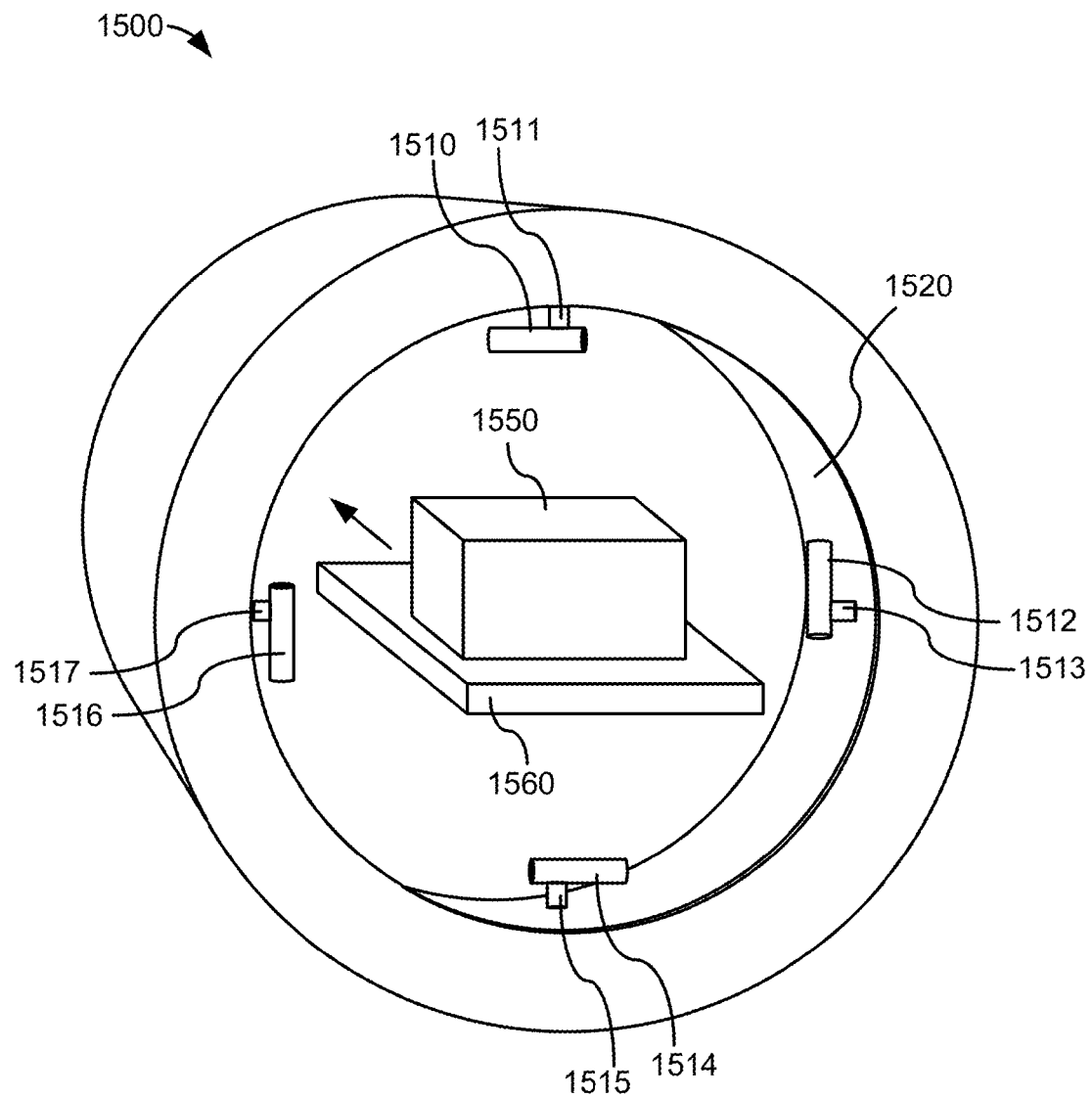
FIG. 15 is a schematic block diagram of a seventh APNR system having multiple neutron sources according to another embodiment of the disclosed technology.

FIG. 15 is a schematic diagram illustrating an exemplary inspection system 1500 that includes a conveyor mechanism 1560 (e.g., a conveyor belt) that moves an object from a loading point (not shown) into an interrogation region defined within a ring-shaped array of neutron detectors 1520. The ring-shaped array of neutron detectors 1520 can be implemented in the same manner as the array 1420 in FIG. 14. Also shown in FIG. 15 are four neutron sources 1510, 1512, 1514, 1516 arranged at regular intervals around the ring-shaped array 1520. For ease of illustration, the physical structures for supporting the illustrated components are not shown. One or more additional or fewer neutron sources can be implemented in embodiments of the disclosed technology. Furthermore, the neutron sources can be arranged in different configurations or at different positions in the system 1500. For instance, in certain embodiments, the neutron sources of the system are located on one half of the ring-shaped array 1520. Still further, in certain embodiments, the ring-shaped array 1520 does not form a full ring, but instead forms a partial ring around the conveyor mechanism (e.g., a semicircular or half-circular shape). In such systems, the object can be reoriented in order to obtain additional projection images at different angles. During neutron interrogation, the conveyor mechanism 1560 can slow down or completely stop so that the projection images of the interrogated object (e.g., object 1550) can be generated. The conveyor mechanism of the system 1500 can also be configured to move the interrogated object through multiple interrogation phases. The multiple interrogation phases can include additional neutron interrogation (e.g., using detectors or neutron sources positioned in different arrangements) or can include secondary inspection using a different technique (e.g., an x-ray inspection system or neutron interrogation technique using gamma-ray detectors).

Figure 16:
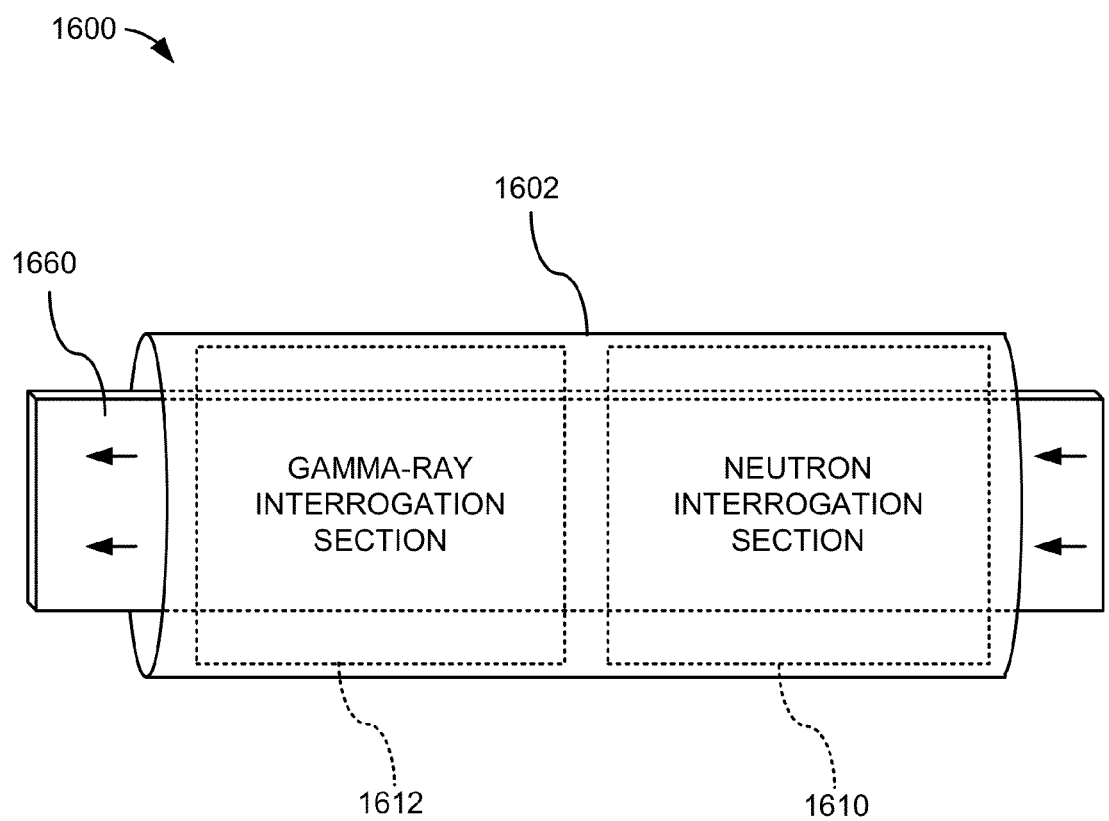
FIG. 16 is a schematic block diagram of a multiple-interrogation-phase APNR system having multiple neutron sources according to another embodiment of the disclosed technology.

FIG. 16 is a schematic block diagram illustrating a top view of an exemplary multi-inspection-phase system 1600. In the illustrated embodiment, conveyor mechanism 1660 moves an interrogated object through a main body 1602, which can be a shielded housing enclosing components of the interrogation subsystems. In FIG. 16, conveyor mechanism 1660 first advances an object to be inspected into a neutron interrogation section 1610. The neutron interrogation section 1610 can implement any of the neutron interrogation systems disclosed herein, such as the system 1500 shown in FIG. 15. After neutron interrogation is complete, the conveyor mechanism 1660 can then move the object to a gamma-ray interrogation section 1612. The gamma-ray (e.g., x-ray) interrogation system can be implemented using any suitable gamma-ray system known to those of ordinary skill in the art. Furthermore, the system 1600 can be operated so that while an object is being scanned in the gamma-ray interrogation section 1612, a different object is being scanned in the neutron interrogation section 1610. Although FIG. 16 only shows two different inspection sections, embodiments of the system 1600 can include one or more additional sections (e.g., additional neutron interrogation sections with neutron sources or neutron detectors positioned in different arrangements). Also, the order of interrogation sections can vary from implementation to implementation.

IV. Further Embodiments Comprising Using Multiple Particle Imaging

Any of the disclosed multi-source embodiments can be used together with imaging systems using different source particles. For example, the disclosed technology can be combined with a gamma-ray imaging system. Additionally, in certain embodiments, the gamma-ray imaging system can include a gamma ray source that generates picturization gamma emissions (e.g., gamma rays used to create a projection image) as well as verification gamma emissions (e.g., gamma rays simultaneously generated with the picturization gamma emission but emitted in the opposite direction). By detecting the picturization gamma emissions and verification gamma emissions using positional sensors, the gamma emissions can be "tagged" in position and time so that an image can be constructed using only those detected gamma emissions that are expected. Example gamma ray systems capable of "tagging" gamma emissions (sometimes referred to herein as "tagged gamma ray systems") are disclosed in U.S. Patent Application Publication No. 2012/0001064, filed on Jun. 30, 2010, and entitled "POSITRON EMISSION IMAGING DEVICE AND METHOD OF USING THE SAME" (now U.S. Pat. No. 8,354,651 issued on Jan. 15, 2013), which is hereby incorporated herein by reference. Other known tagged gamma ray systems can be used with any of the embodiments discussed herein as well.

Imaging systems according to the disclosed technology can include neutron imaging systems (having a single neutron source or multiple neutron sources) combined with gamma ray systems (having a single gamma ray source or multiple gamma ray sources). Furthermore, the use of at least one tagged system (e.g., a tagged gamma ray system, a tagged neutron system, or both) allows for the sources in the tagged systems to be operated simultaneously, thereby allowing the system to capture projections of the same interrogation object at the same time (or substantially the same time) from different angles. For example, embodiments of the combined gamma ray interrogation and neutron interrogation systems include any one or more of the following: (a) a single tagged neutron imaging system with a single gamma imaging system; (b) multiple tagged neutron imaging systems with a single gamma imaging system; (c) a single tagged neutron imaging system with a single tagged gamma imaging system; (d) a multiple tagged neutron imaging systems with single tagged gamma imaging system; (e) single tagged neutron imaging system with multiple tagged gamma imaging systems; or (f) multiple tagged neutron imaging systems with multiple tagged gamma imaging systems.

The use of API neutron radiography can improve the results and/or shorten scan times for any of the combined embodiments. For example, the use of API neutron radiography can help shorten scan times in an inspection system (e.g., a cargo container inspection system). Furthermore, the use of an API neutron radiography (whether single source or multiple source) can provide a number of additional possible advantages, including one or more of the following: (a) the electronic collimation provided by API can remove the need for shielding to create a fan beam; (b) the use of time correlation can reduce noise collected from scattered neutrons; (c) in certain implementations, a mask can be used for the alpha particles to create a fan beam; (d) pixelated alpha detectors used with the API neutron system can further remove scatter using both time and space correlation; (e) the use of tagged API enables multiple neutron sources to be used at once; and/or (f) physical collimators can be omitted from the system, leading to a system that is more compact and yet able to have a cone beam (e.g., with API, a full cone image can be captured with scatter removed as if the neutrons were collimated around a particular direction).

For combined systems using tagged gamma sources, the neutron source can be a fission source that allows time correlation with other fission products and a gamma source with matched gamma emissions that depart the source with a known angle. This allows the emissions to be correlate in both time and direction. The combination of a tagged gamma imaging system with a tagged neutron imaging system can offer a number of unique advantages, including any one or more of the following: (a) electronic collimation provided by API removes the need for shielding to create a fan beam; (b) the use of time correlation reduces noise collected from scattered and background gammas; (c) the use of time and space correlation reduces noise collected from scattered and background gammas; and (d) the use of multiple sources allows the system to obtain multiple views at least partially simultaneously.

Figure 18:
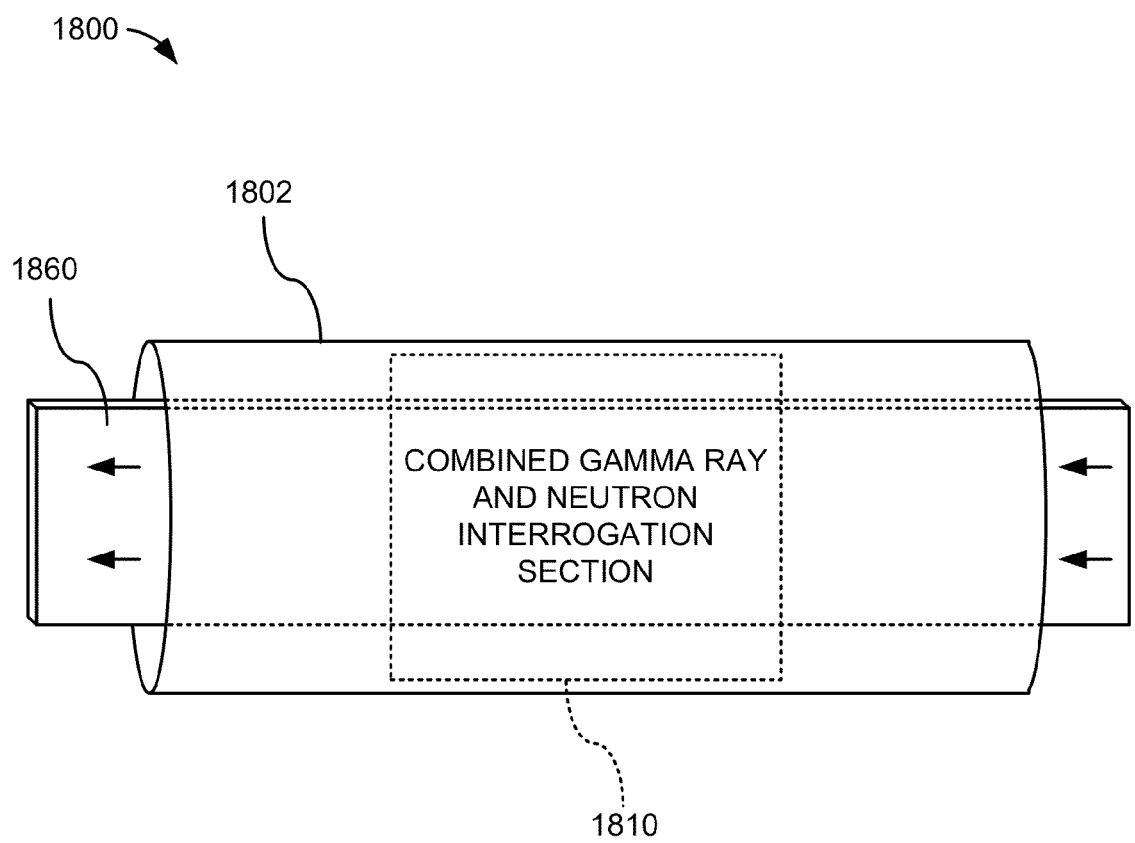
FIG. 18 is a schematic block diagram of an example interrogation system comprising an interrogation region in which neutron and gamma ray imaging are combined.

FIG. 18 is a schematic block diagram illustrating a top view of an exemplary multi-particle inspection system 1800 according to the disclosed technology (e.g., a cargo inspection system). In the illustrated embodiment, a conveyor mechanism 1860 moves an interrogated object through a main body 1802, which can be a shielded housing enclosing components of the interrogation subsystems. In other embodiments, there is no conveyor mechanism.

In FIG. 18, the conveyor mechanism 1860 advances an object to be inspected into a combined gamma ray and neutron interrogation section 1810. The combined gamma ray and neutron interrogation section 1810 can be implemented using any of the multi-particle techniques disclosed herein, such as a combination of a single- or multi-source tagged neutron imaging system together with a single- or multi-source tagged gamma ray imaging system. In certain implementations, a single detector array is used to detect both neutron and gamma rays. In other implementations, however, separate detectors are used to detect the gamma rays from the neutrons. Further, the object being interrogated can be rotated within the system (or the source and detector arrays can be rotated or otherwise moved about the object) using any suitable rotation or actuation mechanism in order to obtain image data from multiple different angles.

By using a tag-based neutron and/or gamma-ray system, neutron image data of an object can be captured at least partially simultaneously with gamma ray image data for the object. This multi-particle approach helps improve the overall time, size, and effectiveness of the inspection system.

In embodiments using combined systems, the imaging processing that is performed is adapted for the presence of both neutrons and gamma rays (e.g., tagged neutrons and/or tagged gamma rays). The modifications to the imaging process are generally straightforward, since the gamma emissions can be differentiated from neutrons either by being detected at a different detector array or as having an energy level characteristic of a gamma emission. The image reconstruction process can involve generating separate projection images for each of the gamma ray and neutron sources, from all of these projection images generating a three-dimensional representation of the object being interrogated. Or, in certain implementations, a separate three-dimensional representation is generated from the neutron projections as from the gamma ray projections.

V. Exemplary Computing Environments

Figure 17:
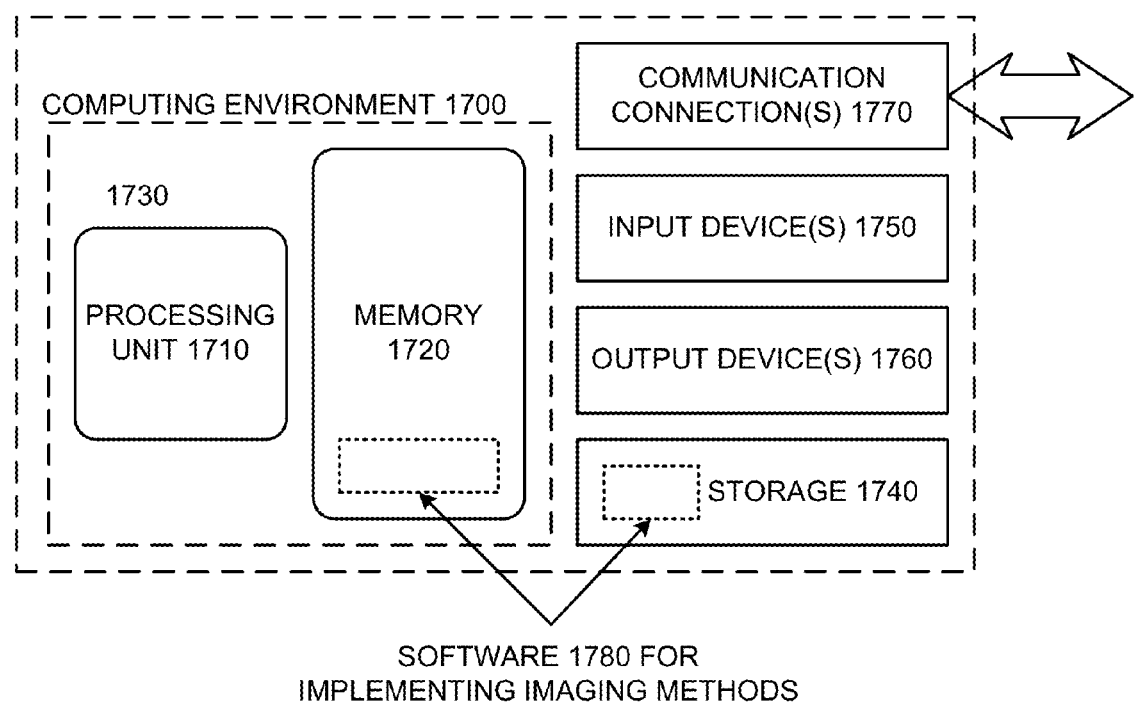
FIG. 17 is a schematic block diagram of a computing hardware architecture that can be used to perform embodiments of the disclosed technology.

FIG. 17 illustrates a generalized example of a suitable computing hardware environment 1700 in which embodiments of the disclosed technology can be implemented. For example, any of the disclosed image processing techniques can be implemented using embodiments of the computing hardware environment 1700. The computing hardware environment 1700 is not intended to suggest any limitation as to the scope of use or functionality of the disclosed technology, as the technology can be implemented in diverse general-purpose or special-purpose computing environments. For example, the image processing techniques described herein can be implemented using multiple computing hardware environments. Each neutron source in a multiple-neutron-source system, for example, can be associated with a separate dedicated computing hardware environment. In such a system, projection images produced from different neutron sources can be processed in parallel using separate computing hardware. Alternatively, two or more projection images can be processed using the same computing hardware.

With reference to FIG. 17, the computing hardware environment 1700 includes at least one processing unit 1710 and memory 1720. In FIG. 17, this most basic configuration 1730 is included within a dashed line. The processing unit 1710 executes computer-executable instructions and may be a real or a virtual processor. In a multi-processing system, multiple processing units execute computer-executable instructions to increase processing power. The memory 1720 can be volatile memory (e.g., registers, cache, RAM, DRAM, SRAM), non-volatile memory (e.g., ROM, EEPROM, flash memory), or some combination of the two. The memory 1720 stores software 1780 for implementing one or more of the image processing techniques. For example, the memory 1720 can store software 1780 for implementing any of the disclosed methods and their accompanying user interfaces.

The computing hardware environment can have additional features. For example, the computing hardware environment 1700 includes a storage device 1740, one or more input devices 1750, one or more output devices 1760, and one or more communication connections 1770. An interconnection mechanism (not shown) such as a bus, controller, or network interconnects the components of the computing hardware environment 1700. Typically, operating system software (not shown) provides an operating environment for other software executing in the computing hardware environment 1700, and coordinates activities of the components of the computing hardware environment 1700.

The storage device 1740 is a type of non-volatile memory and can be removable or non-removable. The storage device 1740 includes, for instance, magnetic disks (e.g., hard drives), magnetic tapes or cassettes, optical storage media (e.g., CD-ROMs or DVDs), or any other tangible non-transitory storage medium that can be used to store information and which can be accessed within or by the computing hardware environment 1700. The storage device 1740 can also store the software 1780 for implementing any of the described techniques.

The input device(s) 1750 can be a touch input device such as a keyboard, mouse, touch screen, pen, trackball, a voice input device, a scanning device, or another device that provides input to the computing environment 1700. The output device(s) 1760 can be a display device, touch screen, printer, speaker, CD-writer, or another device that provides output from the computing environment 1700.

The communication connection(s) 1770 enable communication over a communication medium to another computing entity. The communication medium conveys information such as computer-executable instructions, any of the intermediate or final messages or data used in implementing embodiments of the disclosed technology. For example, signals from the alpha particle detectors or neutron detectors in any of the disclosed systems can be received at the communication connection(s) 1770 after appropriate amplification, filtering, or analog-to-digital conversion. By way of example, and not limitation, communication media include wired or wireless techniques implemented with an electrical, optical, RF, infrared, acoustic, or other carrier.

The various methods disclosed herein (e.g., the image processing methods) can be described in the general context of computer-executable instructions stored on one or more computer-readable media. Computer-readable media are any available media that can be accessed within or by a computing environment. By way of example, and not limitation, with the computing hardware environment 1700, computer-readable media include tangible non-transitory computer-readable media such as memory 1720 and storage 1740. The various methods, systems, and interfaces disclosed herein can also be described in the general context of computer-executable instructions, such as those included in program modules, being executed in a computing environment on a target real or virtual processor. Generally, program modules include routines, programs, libraries, objects, classes, components, data structures, etc. that perform particular tasks or implement particular abstract data types. The functionality of the program modules may be combined or split between program modules as desired in various embodiments. Computer-executable instructions for program modules may be executed within a local or distributed computing environment.

Having illustrated and described the principles of the illustrated embodiments, it will be apparent to those skilled in the art that the embodiments can be modified in arrangement and detail without departing from such principles. For example, in certain embodiments, physical collimators can be used to shape the neutron beam of one or more of the neutron source in certain embodiments of the disclosed technology. Furthermore, any of the disclosed system can be used in conjunction with a gamma-ray interrogation system such that both gamma-ray and neutron interrogation of an object occur at least partially simultaneously. Additionally, in certain embodiments of the disclosed technology, any one or more of the multiple neutron sources can be in motion during the neutron interrogation and imaging process. In particular implementations, for instance, one or more of the neutron sources (or the interrogation region) are rotated so that the resulting scan of the interrogation region is a spiral scan.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. An imaging system, comprising:
   a first neutron source;
   a first array of one or more alpha particle detectors configured to detect alpha particles associated with neutrons generated by the first neutron source;
   a second neutron source;
   a second array of one or more alpha particle detectors configured to detect alpha particles associated with neutrons generated by a second neutron source;
   one or more neutron detectors positioned to detect at least some of the neutrons generated by the first and second neutron sources;
   a gamma ray source;
   an array of one or more verification gamma ray detectors configured to detect verification gamma rays associated with gamma rays generated by the gamma ray source;
   one or more gamma ray detectors configured to detect at least some of the gamma rays generated by the gamma ray source; and
   an interrogation region configured to hold an object to be interrogated by neutrons from the first and second neutron sources and by gamma rays from the gamma ray source, the interrogation region being located between the first and second neutron sources, the gamma ray source, the one or more neutron detectors, and the one or more gamma ray detectors.

2. The imaging system of claim 1, wherein the gamma ray source is a first gamma ray source, the array of one or more verification gamma ray detectors is a first array of one or more verification gamma ray detectors, and
   wherein the imaging system further comprises:
      a second gamma ray source;
      a second array of one or more verification gamma ray detectors configured to detect verification gamma rays generated by the second gamma ray source.

3. The imaging system of claim 1, further comprising an image processing system coupled to the first and second arrays of one or more alpha particle detectors, the one or more neutron detectors, the array of one or more verification gamma ray detectors, and the one or more gamma ray detectors,
   the image processing system being configured to generate an image of an object positioned in the interrogation region, the generated image being based at least in part on the observed number of tagged neutrons detected by the one or more neutron detectors and the observed number of tagged gamma rays detected by the one or more gamma ray detectors.

4. The imaging system of claim 1, wherein the neutrons generated by the first and second neutron sources are uncollimated and form neutron cone beams.

5. A method, comprising:
   interrogating an object with a plurality of neutrons and a plurality of gamma rays using the system of claim 1, at least some of the neutrons and gamma rays being generated during a same time period;
   detecting one or more neutrons and one or more gamma rays; and
   generating an image of the object based at least in part on the detected neutrons and the detected gamma rays.

6. The method of claim 5, wherein a first portion of the neutrons is generated from the first neutron source and a second portion of the neutrons is generated from the second neutron source.

7. The method of claim 6, wherein the first neutron source and the second neutron source are uncollimated.

8. The method of claim 5, wherein the gamma ray source is a first gamma ray source, and wherein a first portion of the gamma rays is generated from the first gamma ray source and a second portion of the gamma rays is generated from a second gamma ray source.

9. The method of claim 5, wherein the generating the image of the object comprises generating projection images from the detected neutrons and the detected gamma rays, the projection images including a first projection image generated from the detected neutrons and a second projection image generated from the gamma rays.

10. A method, comprising:
    generating, at a gamma emission source, a gamma emission and a verification gamma emission associated with the gamma emission;
    detecting the verification gamma emission at a position on a verification gamma emission detector;
    generating, at a first neutron source, a first neutron and a first associated particle;
    detecting the first associated particle at a position on a first associated particle detector;
    generating, at a second neutron source, a second neutron and a second associated particle, the second neutron source being different than the first neutron source;
    detecting the second associated particle at a position on a second associated particle detector, the second associated particle detector being different than the first associated particle detector;

detecting the gamma emission at a gamma emission detector;

detecting the first neutron at a neutron detector; and determining a path of the gamma emission through an interrogated object and a first path of the first neutron through the interrogated object, the determination of the path of the gamma emission being based on the position at which the verification gamma emission is detected on the verification gamma emission detector, and the determination of the first path of the first neutron being based on the position at which the first associated particle is detected on the first associated particle detector.

11. The method of claim 10, wherein the gamma emission is a first gamma emission, the verification gamma emission is a first verification gamma emission, the gamma emission source is a first gamma emission source, and the path of the gamma emission through the interrogated object is a first path of the gamma emission, and wherein the method further comprises:

generating a second gamma emission and a second verification gamma emission associated with the second gamma emission at a second gamma emission source, the second gamma emission source being different than the first gamma emission source; and detecting the second verification gamma emission at a position on a second verification gamma emission detector, the second verification gamma emission detector being different than the first verification gamma emission detector.

12. The method of claim 11, further comprising determining a path of the second gamma emission through the interrogated object, the determination of the path of the second gamma emission being based on the position at which the second verification gamma emission is detected on the second verification gamma emission detector.

13. The method of claim 11, wherein the first gamma emission, the second gamma emission, and the neutron are detected at the same time or substantially the same time.

14. The method of claim 10, wherein the method further comprises determining a second path of the second neutron through the interrogated object, the determination of the second path of the second neutron being based on the position at which the second associated particle is detected on the second associated particle detector.

15. The method of claim 10, wherein the gamma emission, the first neutron, and the second neutron are detected at the same time or substantially the same time.

16. The method of claim 10, wherein the gamma emission detector and the neutron detector are part of a single array of detectors.

17. One or more non-transitory computer-readable media storing computer-executable instructions which when executed by a computer cause the computer to perform a method, the method comprising:

(a) in connection with a tagged neutron system, receiving data from two or more alpha particle detectors, including data from a first alpha particle detector indicating times at which a first set of alpha particles are detected by the first alpha particle detector and data from a second alpha particle detector indicating times at which a second set of alpha particles are detected by the second alpha particle detector, wherein the first set of alpha particles are associated with a first set of neutrons generated by a first neutron source, and wherein the second set of alpha particles are associated with a second set of neutrons generated by a second neutron source;

receiving data from one or more neutron detectors indicating times at which neutrons are detected by the one or more neutron detectors;

identifying the neutrons detected by the one or more neutron detectors as being either neutrons emitted from the first neutron source or neutrons emitted from the second neutron source based at least in part on the data from the first alpha particle detector and the data from the second alpha particle detector; and (b) in association with a tagged gamma emission system, receiving data from two or more verification gamma emission detectors, including data from a first verification gamma emission detector indicating times at which a first set of verification gamma emissions are detected by the first verification gamma emission detector and data from a second verification gamma emission detector indicating times at which a second set of verification gamma emissions are detected by the second verification gamma emission detector, wherein the first set of verification gamma emissions are associated with a first set of picturization gamma emissions generated by a first gamma emission source, and wherein the second set of verification gamma emissions are associated with a second set of picturization gamma emissions generated by a second gamma emission source;

receiving data from one or more picturization gamma emission detectors indicating times at which picturization gamma emissions are detected by the one or more gamma emission detectors; and identifying the picturization gamma emission detected by the one or more picturization gamma emission detectors as being either picturization gamma emissions emitted from the first gamma emission source or picturization gamma emissions emitted from the second gamma emission source based at least in part on the data from the first verification gamma emission detector and the data from the second verification gamma emission detector.

18. The one or more computer-readable media of claim 17, wherein the first set of neutrons, the second set of neutrons, the first set of picturization gamma emissions, and the second set of picturization gamma emission are all generated at least partially during a same time period and are used to interrogate an object being imaged during the same time period.

* * * * *